US011291939B1

(12) United States Patent
Luthe

(10) Patent No.: US 11,291,939 B1
(45) Date of Patent: Apr. 5, 2022

(54) ULTRA-FINE PARTICLE AGGREGATION, NEUTRALIZATION AND FILTRATION

(71) Applicant: Smart Material Printing B.V., Enschede (NL)

(72) Inventor: Gregor Luthe, Gronau (DE)

(73) Assignee: Smart Material Printing B.V., Enschede (NL)

( * ) Notice: Subject to any disclaimer, the term of this patent is extended or adjusted under 35 U.S.C. 154(b) by 0 days.

(21) Appl. No.: 17/471,610

(22) Filed: Sep. 10, 2021

Related U.S. Application Data

(60) Provisional application No. 63/221,289, filed on Jul. 13, 2021.

(51) Int. Cl.
  *A61L 9/20* (2006.01)
  *B01D 49/00* (2006.01)
  (Continued)

(52) U.S. Cl.
  CPC ............ *B01D 46/0028* (2013.01); *A61L 9/20* (2013.01); *B01D 46/0039* (2013.01); *B01D 49/006* (2013.01); *B01D 51/02* (2013.01); *B01D 51/08* (2013.01); *H04R 17/00* (2013.01); *B01D 2279/65* (2013.01); *B01J 19/10* (2013.01);
  (Continued)

(58) Field of Classification Search
  CPC ............ B01D 46/0028; B01D 46/0039; B01D 51/02; B01D 51/08; B01D 2279/65; B01D 53/34; B01D 49/006; A61L 9/20; A61L 9/205; H04R 17/00; B03D 3/04; C02F 1/32; C02F 1/325; C02F 1/36; C02F 2201/322; C02F 2201/3222; C02F 2201/3225; C02F 2201/3227; C02F 2201/3228; B01J 19/10
  See application file for complete search history.

(56) References Cited

U.S. PATENT DOCUMENTS 4,307,964 A   12/1981   Dudgeon et al.
4,759,775 A   7/1988    Peterson et al.
(Continued)

FOREIGN PATENT DOCUMENTS

CA   2097070      5/1992
CN   104363996    2/2015
(Continued)

OTHER PUBLICATIONS

RU2740899C1_ENG (Espacenet machine translation of Golykh) (Year: 2021).*
(Continued)

*Primary Examiner* — Jonathan Miller
*Assistant Examiner* — Gabriel E Gitman
(74) *Attorney, Agent, or Firm* — Weiss & Arons LLP

(57) ABSTRACT

This disclosure relates to aggregating, neutralizing, and filtering ultra-fine particles in fluids such as air and water. Fluid may be drawn from an ambient environment into a neutralization chamber. Within the neutralization chamber, particles in the fluid may be agglomerated. An acoustic field may be applied to the fluid to agglomerate the particles. The agglomerated particles may be exposed to light. The light may denature or deactivate the agglomerated particles. The agglomerated and inert particles may be passed through a filter. After agglomeration and neutralization, the fluid may be released back into the ambient environment.

15 Claims, 17 Drawing Sheets

(51) Int. Cl.
| | |
|---|---|
| *H04R 17/00* | (2006.01) |
| *B01D 46/00* | (2022.01) |
| *B01D 51/02* | (2006.01) |
| *B01D 51/08* | (2006.01) |
| *H01L 25/075* | (2006.01) |
| *C02F 1/32* | (2006.01) |
| *B01J 19/10* | (2006.01) |
| *H01L 27/00* | (2006.01) |

(52) U.S. Cl.
CPC ............ *C02F 1/32* (2013.01); *C02F 2201/32* (2013.01); *C02F 2201/3222* (2013.01); *C02F 2201/3227* (2013.01); *H01L 25/0753* (2013.01); *H01L 27/00* (2013.01)

(56) References Cited

U.S. PATENT DOCUMENTS

| | | | |
|---|---|---|---|
| 5,225,089 | A | 7/1993 | Benes et al. |
| 5,527,460 | A | 6/1996 | Trampier et al. |
| 5,769,913 | A | 6/1998 | Gallego et al. |
| 5,827,350 | A | 10/1998 | Magill et al. |
| 5,902,489 | A | 5/1999 | Yasuda et al. |
| 5,902,849 | A | 5/1999 | Heucher et al. |
| 6,224,652 | B1 | 5/2001 | Caperan et al. |
| 6,322,614 | B1 * | 11/2001 | Tillmans ............... F24F 7/065 96/16 |
| 6,447,574 | B1 | 9/2002 | Frier, Jr. et al. |
| 7,674,620 | B2 | 3/2010 | Totey et al. |
| 7,674,630 | B2 | 3/2010 | Siversson |
| 8,454,716 | B2 | 6/2013 | Sedillo |
| 2003/0200864 | A1 | 10/2003 | Meegan, Jr. |
| 2004/0226437 | A1 | 11/2004 | Stenersen et al. |
| 2008/0181828 | A1 | 7/2008 | Kluck |
| 2011/0171090 | A1 * | 7/2011 | Johnson ................. A61L 9/22 423/210 |
| 2012/0267288 | A1 | 10/2012 | Chen et al. |
| 2015/0265961 | A1 | 9/2015 | Davey et al. |
| 2016/0059206 | A1 * | 3/2016 | Chen ..................... G01N 1/4077 210/748.05 |
| 2018/0346348 | A1 * | 12/2018 | Collins .................... C02F 1/36 |
| 2019/0070528 | A1 * | 3/2019 | Luthe .................. B01D 21/283 |
| 2020/0009286 | A1 * | 1/2020 | Zarcone ................. H05B 47/19 |
| 2021/0341370 | A1 | 11/2021 | Luthe et al. |

FOREIGN PATENT DOCUMENTS

| | | | |
|---|---|---|---|
| CN | 205669422 | | 11/2016 |
| DE | 19513603 | | 10/1996 |
| DE | 19846115 | | 4/2000 |
| DE | 69705226 | | 9/2001 |
| DE | 69628389 | | 4/2004 |
| DE | 102009036948 | | 2/2011 |
| EP | 0773055 | A2 | 5/1997 |
| EP | 0773055 | A3 | 6/1997 |
| EP | 0923410 | | 6/2001 |
| EP | 0773055 | | 5/2003 |
| GB | 460795 | | 2/1937 |
| JP | S59154151 | | 9/1984 |
| JP | 07047259 | | 2/1995 |
| JP | H09122480 | | 5/1997 |
| JP | 2004042044 | | 2/2004 |
| RU | 2740899 | C1 * | 1/2021 ............. B01D 51/08 |
| WO | W092/09354 | | 6/1992 |
| WO | WO2011/152796 | | 12/2011 |
| WO | WO2017/153038 | | 9/2017 |
| WO | WO2017/154804 | | 9/2017 |
| WO | WO2020/078577 | | 4/2020 |
| WO | WO2020/164792 | | 8/2020 |

OTHER PUBLICATIONS

European Patent Office (as International Searching Authority), International Search Report for International Application No. PCT/EP2019/000293, dated Jan. 22, 2020. (German language original and uncertified English translation).

K. W. Lee, et al., "On the Minimum Efficiency and the Most Penetrating Particle Size for Fibrous Filters," Journal of the Air Pollution Control Association, vol. 30, No. 4, pp. 377-381, Apr. 1980.

Günter Oberdörster, et al., "Nanotoxicology, An Emerging Discipline Evolving from the Studies of Ultrafine Particles," Environmental Health Perspectives, vol. 113, No. 7, pp. 823-839, Jul. 2005.

Günter Oberdörster, et al., "Toxicology of nanoparticles: A historical perspective," Nanotoxicology, vol. 1, No. 1, pp. 2-25, Mar. 2007.

European Patent Office (as International Searching Authority), International Search Report for International Application No. PCT/EP2017/000285, dated Sep. 25, 2017. (German Tanguage original and uncertified English translation).

German Patent and Trade Mark Office, Office Action for German Patent Application No. 102016002599.9, dated Nov. 15, 2016. (German language original and partial uncertified English translation).

German Patent and Trade Mark Office, Office Action for German Patent Application No. 102016002600.6, dated Dec. 2, 2016. (German language original and partial uncertified English translation).

Sergey Kapishnikov, et al., "Continuous particle size separation and size sorting using ultrasound in microchannel," Journal of Statistical Mechanics: Theory and Experiment, vol. 2006, Issue 01, p. 01012, IOP Publishing Ltd, https://doi.org/10.1088/1742-5468/2006/01/P01012, Jan. 2006.

European Patent Office (as International Searching Authority), Written Opinion for International Application No. PCT/EP2005/000285, dated Sep. 25, 2017. (German language original and uncertified English translation).

Brazil Patent and Trademark Office, Office Action for Brazilian Patent Application No. BR112018067809-0, dated May 6, 2021. (Portuguese language original and partial uncertified English translation).

United States Patent and Trademark Office, Office Action in U.S. Appl. No. 16/082,521, filed Sep. 21, 2021.

Korean Intellectual Property Office, Office Action in Korean Application No. 10-2018-7028414, dated Oct. 28, 2021. (uncertified English language translation).

Japan Patent Office, Office Action in Japanese Patent Application No. 2018-547927, dated Feb. 17, 2021. (uncertified English language translation).

Japan Patent Office, Office Action in Japanese Patent Application No. 2018-547927, dated Jul. 13, 2021. (uncertified English language translation).

State Intellectual Property Office of People's Republic of China, First Office Action in Chinese Patent Application No. 201780027747.8, dated Aug. 19, 2020. (uncertified English Tanguage translation).

State Intellectual Property Office of People's Republic of China, Second Office Action in Chinese Patent Application No. 201780027747.8, dated May 10, 2021. (uncertified English Tanguage translation).

State Intellectual Property Office of People's Republic of China, Third Office Action in Chinese Patent Application No. 201780027747.8, dated Sep. 29, 2021. (uncertified English Tanguage translation).

Vladimir N. Khmelev et al., "The Limits of Fine Particle Ultrasonic Coagulation," Symmetry 2021, 13, 1607, https://doi.org/10.3390/sym13091607, MDPI (https://www.mdpi.com/journal/symmetry), Sep. 1, 2021.

Australian Government—IP Australia, Examination Report No. 1 in Australian Patent Application No. 2017229176, dated Nov. 30, 2021.

* cited by examiner

800 ↘  802 ↘

| ID | Name | Designator | Footprint | Quantity | Manufacturer Part | Manufacturer |
|---|---|---|---|---|---|---|
| 1 | LTST-C171KGKT | LED13 | LED0805-RD | 1 | LTST-C171KGKT | LITEON |
| 2 | 100nF | C18,C11,C19,C12,C15,C14,C13 | C0805 | 7 | CC0805KRX7R9BB104 | YAGEO |
| 3 | DMN2046 | Q3,Q2,Q6,Q5 | SOT-23-3_L2.9-W1.6-P1.90-LS2.8-BR | 4 | DMN2046U-7 | Diodes Incorporated |
| 4 | X3025WRS-2*04D-LPSW | CN3 | CONN-SMD_8P-H-R2-C4-P3.00-BR_X3025WRS | 1 | X3025WRS-2*04D-LPSW | XKB Enterprise |
| 5 | FIDUCIALS | F1,F2,F3,F4 | FIDUCIAL 1MM | 4 | | |
| 6 | 2.2uF | C8 | C1206 | 1 | CC1206KKX7R7BB225 | YAGEO |
| 7 | 321010 | CN2,CN1 | CONN-SMD_10P-P2.54_B-3000N10P-0110 | 2 | 321010MG0CBK00A02 | JILN |
| 8 | 16MHz | X1,X2 | OSC-SMD_4P-L3.2-W2.5-BL | 2 | X1E000021011900 | EPSON |
| 9 | L293DD013TR | U60,U61 | SOP-20_L13.2-W7.8-P1.27-LS10.4-BL | 2 | L293DD013TR | STMicroelectronics |
| 10 | TZ35UVA+UVC06-003 | LED11,LED10,LED9,LED8,LED7,LED3,LED6,LED1,LED 4,LED5,LED12,LED2 | LED-SMD_5P-L3.5-W3.5_TZ35UVA | 12 | TZ35UVA+UVC06-003 | TUOZHAN |
| 11 | EMC2301-1-ACZL-TR | MC3 | MSOP-8_L3.0-W3.0-P0.65-LS5.0-BL | 1 | EMC2301-1-ACZL-TR | MICROCHIP |
| 12 | 1uF | C21,C7,C20 | C0805 | 3 | CC0805KKX7R8BB105 | YAGEO |
| 13 | 22uF | C10,C6 | C0805 | 2 | GRM21BR61E226ME44L | MuRata |
| 14 | ZXMP3A16GTA | Q7 | SOT-223-3_L6.5-W3.4-P2.30-LS7.0-BR | 1 | ZXMP3A16GTA | Diodes Incorporated |
| 15 | 10uF | C9,C5,C16,C17 | C1206 | 4 | CL31A106KBHNNNE | SAMSUNG |
| 16 | 4.7K | R6,R16,R13,R9,R18,R17,R2, | R0805 | 18 | 0805W8F4701T5E | UniOhm |

| ID | Name | Designator | Footprint | Quantity | Manufacturer Part | Manufacturer |
|---|---|---|---|---|---|---|
| | | R12,R1,R15, R11,R3,R10, R8,R4,R14,R5, R38 | | | | |
| 17 | 47053-1000 | CN7 | CONN-TH_47053-1000 | 1 | 47053-1000 | MOLEX |
| 18 | 56 | R32,R34,R22, R23,R25,R28, R29,R35,R31, R19,R20,R26 | R2512 | 12 | CR2512F56RE042W | Ever Ohms Tech |
| 19 | TAG-CONNECT-TC-2030 SPI | CN4,CN5 | TAG-CONNECT_TC2030-IDC-NL | 2 | TAG-CONNECT TC-2030 | |
| 20 | AP2204K-3.3TRG1 | LDO2 | SOT-23-5_L3.0-W1.7-P0.95-LS2.8-BR | 1 | AP2204K-3.3TRG1 | DIODES |
| 21 | PANASONIC | R7 | R0603 | 1 | ERTJ1VA101J | PANASONIC |
| 22 | AZ1117H-5.0TRE1 | LDO3,LDO1 | SOT-223-3_L6.5-W3.4-P2.30-LS7.0-BR | 2 | AZ1117H-5.0TRE1 | DIODES |
| 23 | 22pF | C3,C4,C2,C1 | C0805 | 4 | HGC0805G022OJ500NTGJ | Chinocera |
| 24 | 10mmPiezo | U16,U17,U18, Ul9,U20,U21, U22,U23,U24, U25,U26,U27, U4,U5,U34, U35,U36, U37,U38,U39, U40,U41,U42, U43,U44,U45, U46,U47,U48, U49,U50,U51, U52,U53, U54,U55,U56, U57,U6,U7, U8,U9,U10, U11,U12,U13, U14,U15 | 10MMPIEZO | 48 | | Murata |
| 25 | 150 | R37 | R0805 | 1 | 0805W8J0151T5E | UniOhm |
| 26 | 39 | R21,R24,R27, R36,R33,R30 | R2512 | 6 | CR2512F39RE042W | Ever Ohms Tech |

FIG. 8B

ULTRA-FINE PARTICLE AGGREGATION, NEUTRALIZATION AND FILTRATION

CROSS REFERENCE TO RELATED APPLICATION

This application is a nonprovisional of U.S. Patent Application No. 63/221,289 filed on Jul. 13, 2021, which is hereby incorporated by reference herein in its entirety.

FIELD OF TECHNOLOGY

This disclosure relates to filtering and neutralizing ultra-fine particles in fluids such as air and water.

BACKGROUND

Air pollution is one of the world's largest environmental health threats, causing 8.8 million deaths every year. Exemplary air pollution may include pathogens and allergens, such as viruses, fungal spores, bacteria and pollen. Exemplary air pollution may include industrial pollutants, vehicle fumes and toxic gases, such as ozone, nitrous oxide and sulfur dioxide.

Conventional solutions for removing pollutants include passing fluid through a filter. Filters are typically classified according to their separation efficiency. For example, high-performance particle filters (EPA=Efficient Particulate Air Filter), are capable of filtering particle sizes of 100 nanometers ("nm") or larger. Suspended matter filters (HEPA=High-Efficiency Particulate Air Filter) are also capable of filtering particles of 100 nm or larger. High-performance suspended particulate matter filters (ULPA=Ultralow Penetration Air Filter) are capable of filtering particles 50 nm or greater.

However, such specialized filters are expensive and are not readily available. More conventional filters are only capable of catching particles 300 nm or greater. For example, a conventional automobile cabin filter will only catch particles 500 nm and larger. In any case, even using specialized filters, there are no filters available for catching particles that are 1-50 nm in size.

Furthermore, various filtering techniques are employed by specialized filters. Filter techniques may include a diffusion effect. Very small particles (particle size 50 nm to 100 nm) do not follow the fluid flow. These very small particles have a trajectory similar to Brownian motion due to collisions with the gas or other molecules in the fluid. When these very small particles pass through a filter, they collide and adhere with the filter fibers. This filtering technique may also be referred to as a diffusion regime or diffusion effect.

Filtering techniques include a blocking effect. Small particles (particle size 100 nm to 500 nm) follow the fluid flow. When these small particles pass through a filter, they adhere to the filter fibers. These small particles may adhere to the filter fibers even when they come close to the fibers, and without directly contacting the fibers. This effect is also known as the interception regime.

Filtering techniques include the inertia effect. Larger particles (particle size 500 nm to >1 micrometer ("µm")) do not follow the fluid flow around filter fibers. These relatively large particles collide with the filter fibers due to the inertia and adhere to the fibers. This effect is also known as the inertial impact regime.

Particles with a size of 200 nm to 400 nm are the most difficult to separate using fibrous filters. Particles in this size range are known as Most Penetrating Particle Size ("MPPS"). Filter efficiency typically drops to 50% for particles in the MPPS size range. Larger and smaller particles may separate better due to their physical properties.

Fibrous filter efficiency also degrades over time. As more fluid is continuously pushed through a fibrous filter, the likelihood that particles will penetrate through the filter increases. Particles that may diffuse into and within a filter, over time, may diffuse out of the filter.

Additionally, relatively denser filters, such as an ULPA Filter improve the likelihood of catching undesirable particles. However, such dense filters also increase the cost and lower the energy efficiency of moving fluid through the filter. Just as the denser filter impedes the flow of unwanted particles, the denser filter also impedes the flow of the desirable fluid. Increased power must be provided to move fluid through systems that utilize denser filters. Attempting to move fluid through dense filters also increase noise, up to 80 decibels ("dB"), generated by these systems.

Even the most effective fibrous filters are not capable of catching nanoparticles with an average particle size of 1 nm to <50 nm. Particles in this size range are easily deposited in the bronchi and alveoli of human lungs and are generally associated with high mortality and toxicity rates. Particles that cause diseases such as asthma, bronchitis, arteriosclerosis, arrhythmia, dermatitis, autoimmune diseases, cancer, Crohn's disease or organic failure are in the size range of 1 nm to <50 nm.

Filters (e.g., HEPA/ULPA) for removing pollutants from a fluid may be used in conjunction with irradiation of the fluid with ultraviolet ("UV") light. Such system may only be effective on particles larger than 300 nm. Such systems may also utilize UV light at a wavelength that produces toxic ozone gas. Such systems still require regular and expensive filter replacements. Used filters add refuse to landfills and changing the filter may cause exposure to particles trapped within the filter.

Filters (e.g., HEPA/ULPA) may be used in conjunction with ionization or exposure of the fluid to hydroxyl radicals. However, these technologies either use or create highly toxic and carcinogenic chemicals. Government agencies (e.g., U.S. Environmental Protection Agency) do not recommended these system for indoor use. These systems also suffer from the drawbacks of regular filter replacement.

The smaller a particle is, the more likely the particle will be transmitted as an aerosol in air and stay airborne longer. For example, particles having a nucleus of 1 to 5 micrometers ("µm") can remain airborne for many minutes or even hours. Accordingly, it is desirable to provide improved techniques for filtering and neutralizing particles 1 nm or larger.

BRIEF DESCRIPTION OF THE DRAWINGS

The objects and advantages of this disclosure will be apparent upon consideration of the following disclosure, taken in conjunction with the accompanying drawings, in which like reference characters refer to like parts throughout, and in which:

FIGS. 8A-8C show illustrative apparatus in accordance with principles of the disclosure;

DETAILED DESCRIPTION

Figure 1:
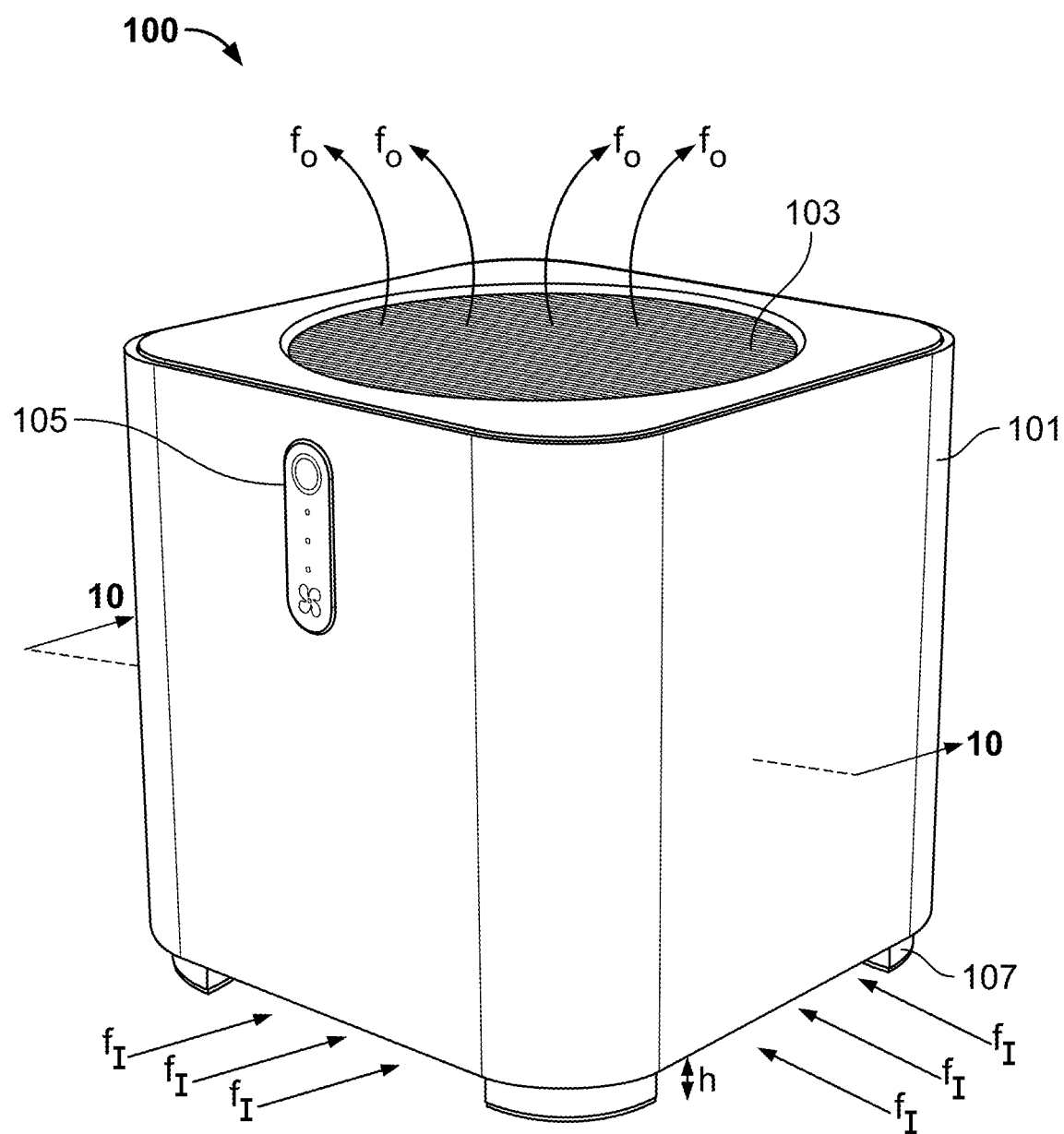
FIG. 1 shows an illustrative apparatus in accordance with principles of the disclosure.

An apparatus for denaturing particles in fluid is provided. The particles may be ultra-fine particles that are smaller than 100 nanometers ("nm"). The particles may be smaller than 300 nm. The fluid may be air. The fluid may be water. The fluid may be industrial gases, raw gases, medical gases, exhaust gases, water, wastewater, organic solvents, solutions, edible oils, lubricating oils, gear oils, crude oils, foods, coolants, gels, dispersions, suspensions, emulsions and/or any fluid.

Particles in the fluid may have different shapes, sizes and or densities. Particles in the fluid may be nanometers, micrometers, millimeters, centimeters and/or decimeters in size. Particles may be distributed homogeneously and/or non-homogeneously within the fluid.

The apparatus may denature more than 80%, and in some cases 99.9%, of all viruses in the fluid. The apparatus may kill more than 80%, and in some cases 99.9%, of all bacteria in the fluid. The apparatus may denature small viruses such as COVID-19 or Influenza. The apparatus may neutralize ultra-fine particles that are 10 nm in size. The apparatus may operate without a filter. The apparatus may operate in conjunction with conventional filters and filtering techniques.

The apparatus may reduce energy required to apply conventional filtering techniques to a fluid. For example, typical ULPA/HEPA filters are dense, which causes a high drop in pressure across the filers and requires higher levels of energy to push air or other fluids through the filters. The apparatus may effectively agglomerate particles before the fluid is passed through a filter. Because particles in the fluid have been agglomerated by the apparatus, a more porous filter can be used effectively. A more porous filter may require less energy to push air or other fluids through the filter.

In addition, the apparatus described herein may reduce clogging or replacement frequency of any filters (e.g., HEPA filters) that are used in connection with the apparatus. The apparatus may reduce the total number of particles in a fluid thereby reducing the need for dense filters and extending the usable life of any filters used in connection with the apparatus.

The apparatus may utilize ultrasonic waves in combination with UV-C or other light radiation. The ultrasonic waves may agglomerate small (e.g., 10 nm) particles in the fluid. The agglomerated particles may be 300 nm or larger. For example, resultant agglomerated particles may be 2,500 nm. The larger, agglomerated particles may be more vulnerable to denaturation when exposed to light.

Additionally, exposing the larger, agglomerated particles to light may increase energy absorbed by the agglomerated particles. Heat absorption of a particle may be a function of the particle's size. Increasing the particle size may cause a corresponding increase in energy absorbed when the agglomerated particles are exposed to light. The increased energy absorption may heat the agglomerated particles. Increasing particle size through agglomeration may increase the level of light and corresponding energy absorption, increasing the amount of heat applied to particles in the fluid.

Furthermore, exposing the larger, agglomerated particles to light may cause the particles to rotate, resonate or vibrate within the peaks/troughs of light waves. This movement of the particles may further increase heating of the particle when exposed to light. The wavelength of the applied light may be coordinated to be slightly larger than the size of the agglomerated particles. More generally, exposing particles in a fluid to light may also makes the particles more "sticky" and enhances efficacy of agglomeration when the fluid is passed through an acoustic field.

The apparatus may not produce hazardous filter waste nor create any dangerous by-products such as ozone. The apparatus may operate at a lower power consumption level comparable to other devices on the market. The apparatus may operate at a noise level of 40 dB (as silent as a refrigerator).

The apparatus may include a neutralization chamber. The apparatus may include electronic circuitry. The electronic circuitry may generate an acoustic field within the neutralization chamber. The acoustic field may include at least one sound wave. The sound wave may be an ultrasonic wave. As the fluid is passed through the neutralization chamber, particles in the fluid are agglomerated by the acoustic field.

The apparatus may include at least one circuit board. The neutralization chamber may be defined, at least in part by a space between two opposing circuit boards. The apparatus may include an inlet. The inlet may allow fluid to enter the neutralization chamber. The fluid may be drawn into the apparatus from the ambient environment through the inlet. The apparatus may include a fan that draws fluid into the inlet from an ambient environment. The fan may push the fluid into the neutralization chamber. The fan may push the fluid out of the neutralization chamber and back into the ambient environment.

A circuit board may contain a sound generator. The sound generator may be one of a plurality of sound generators mounted on the circuit board. A circuit board may contain one or more piezo components. The piezo components may generate one or more sound waves. The circuit board may include a light emitting diode ("LED"). The LED may be one of a plurality of LEDs mounted on the circuit board.

The apparatus may include two or more circuit boards that each include piezo components and LEDs. Two circuit boards may be positioned parallel and opposite each other. The two circuit boards may be separated by a distance of 6-8 centimeters ("cm"). Fluid may flow or be pushed through space between the circuit boards. The space between the circuit boards may define, at least part of, the neutralization chamber.

Piezo components of each circuit board may be aligned with each other. Aligning piezo components of each circuit board may generate a standing sound wave between two opposing and aligned piezo components of each circuit board. Particles within the fluid may be agglomerated at nodes of the standing sound wave. A standing sound wave includes nodes (troughs) and antinodes (peaks). Relative to the antinodes, there is lower or zero pressure at the nodes of a standing sound wave. The lower pressure cause particle agglomeration at or near the nodes.

As the fluid passes nodes of a first standing wave, particles may bind to each other and form larger particles. As the fluid continues to flow through the neutralization chamber and past additional standing sound waves, the agglomerated particles may in turn bind to each other and form even larger particles. Agglomeration may occur for particles sizes of 1 nm to 5000 nm (or larger). Agglomeration may occur for exemplary particles such as bacteria, metal salts, organics, acidic compounds, aerosols and viruses.

An illustrative sound wave may propagate at an angle>0° with respect to the direction fluid flow through the neutralization chamber. The piezo components may be arranged to generate one or more sound waves that propagate at any suitable angle with respect to fluid flow through the neutralization chamber. For example, the angle may be a right angle. Piezo components for generating one or more stationary sound waves may be arranged opposite to each other. In a preferred embodiment, piezo components for generating stationary sound waves are positioned to emit sound waves that propagate perpendicular to a flow of fluid through a neutralization chamber.

Piezo components and sound waves generated by the piezo components may be spaced apart from each other. Within the neutralization chamber, piezo components may be spaced apart from each other along a directional line of fluid flow through the neutralization chamber. A directional line connecting nodes or antinodes of standing sound waves generated by the piezo components may extend in the same direction as, or parallel to, fluid flow through the neutralization chamber.

An illustrative sound wave generated by a circuit board and associated piezo components may have any suitable frequency, shape and/or amplitude. A shape of a generated sound wave may be sinusoidal, sawtooth, rectangular, triangular or any other shape.

Sound waves generated by the piezo components may be dynamically controlled by altering phase or other properties of generated sound waves. Altering phase may allow nodes and antinodes in a generated sound wave to be positioned in preselected locations within the neutralization chamber. Position and location control of nodes and antinodes may be implemented using a combination of Boolean logic gates. The Boolean logic gates may be embedded in the circuit board.

Illustrative piezo components may be configured to generate two or more sounds waves. Each generated sound wave may have different properties. For example, each sound wave may have nodes/antinodes positioned in different locations within the neutralization chamber. Each sound waves may have a different (more or less) number of nodes/antinodes. Sound waves generated within a neutralization chamber may each have different frequencies, shapes and/or amplitudes.

Varying the properties of sound waves generated within the neutralization chamber may increase efficacy of agglomeration of particles within the fluid. Varying the properties of sound waves generated within the neutralization chamber may agglomerate different particles in different spatial regions of the neutralization chamber.

Sound waves generated by the piezo components may have a frequency and/or audible volume that is outside the hearing range of humans and animals. The apparatus may include sound-insulating material that reduces noise produced by the sound waves. The sound insulating material may provide passive noise canceling. The apparatus may include noise-reducing loudspeakers that perform active noise canceling, or noise suppression.

A sound wave generated by the piezo components may be a stationary sound wave. A reflector may be positioned opposite a piezo component. The reflector may reflect the sound wave generated by a piezo component to create a stationary or standing sound wave.

In some embodiments, the apparatus may only include one circuit board. The one circuit board may include an acoustic generator. The acoustic generator may be a microelectromechanical system ("MEMS"), a piezo device, a speaker, horn or any other suitable component for generating a sound wave. Embodiments that include a single circuit board may also include an acoustic reflector or mirror. The acoustic reflector may be positioned opposite the acoustic generator. The acoustic reflector may reflect sound waves generated by the acoustic generator. The reflected and generated sound waves may collectively form a standing sound wave that includes nodes and antinodes. Particles in the fluid may be agglomerated at the nodes and/or antinodes of the standing sound wave.

The apparatus may include at least two circuit boards. The two circuit boards may be positioned parallel and opposite to each other. Each circuit board may include an acoustic generator. For example, a circuit board may include two sound generating piezo components or one sound generating piezo component and one corresponding acoustic reflector. An illustrative acoustic reflector may be constructed from plastic, glass, metal, glass backed with silver, or any suitable material that reflects sound. An illustrative acoustic reflector may have any suitable shape. For example, an acoustic reflector may be parabolic, convex, concave, flat, or have a multi-faceted surface.

The apparatus may include two circuit boards that are positioned opposite and facing each other. The two circuit boards may be positioned such that acoustic generators of each circuit board are aligned with each other. Such aligning may allow the acoustic generators to be tuned such that sound waves produced by the two facing and aligned acoustic generators form a standing sound wave. Aligning the acoustic generators may include ensuring that sound waves produced by the two acoustic generators are in-phase.

Software may be utilized to perform aligning of acoustic generators. Exemplary software may adjust a phase of sound waves produced by an acoustic generator. A circuit board that includes an acoustic generator may be moveable. Software may control movement of the circuit board to adjust a position of the acoustic generator. The software may issue instructions to adjust a position of a first circuit board so that a sound wave produced by acoustic generators of the first circuit board are aligned with sound waves produced by acoustic generators of a second and opposing circuit board.

Acoustic generators of a circuit board may be moveable. For example, the acoustic generators may be MEMS devices. The software may issue instructions to the MEMS device and adjust a propagation direction or other attribute of a sound wave generated by the MEMS device. An acoustic reflector may be moveable. For example, an acoustic reflector may be a MEMS device. Software may control movement of an acoustic reflector.

Two in-phase sound waves may form a standing sound wave that has a larger amplitude than each of the individual sound waves. A larger amplitude may correspond to greater displacement between nodes and antinodes of the resulting standing sound wave. A greater displacement between nodes and antinodes of the standing sound wave may enhance agglomeration of particles at the nodes and/or antinodes.

In some embodiments, an acoustic reflector may be positioned between two acoustic generators. The acoustic reflector may be configured to vibrate or move in response to sound waves emitted from an acoustic generator. For example, an acoustic reflector may be suspended within the neutralization chamber between two acoustic generators. The acoustic reflector may be a flat rigid surface or a flexible surface such as a segment of tape. The acoustic reflector may have two or more reflective surfaces. The acoustic reflector may be moveable within the neutralization chamber.

A first side of the acoustic reflector may reflect sound waves produced by a first acoustic generator. A second side of the acoustic reflector may reflect sound waves produced by a second acoustic generator. The reflection of sound waves produced by the first and second acoustic generators may cause the acoustic reflector to vibrate.

The first side of the acoustic reflector may reflect sound waves generated by the first acoustic generator such that a first standing sound wave is formed between the first side of the acoustic reflector and the first acoustic generator. The second side of the acoustic reflector may reflect sound waves produced by the second acoustic generator such that a second standing sound wave is formed between the second side of the acoustic reflector and the second acoustic generator.

Suspending an acoustic reflector between two acoustic generators may avoid a need to align the two acoustic generators to form a standing sound wave. Sound waves produced by the two acoustic generators may remain out of phase with each other. The intervening acoustic reflector may allow dominant components of each sound wave to be reflected back to the emitting acoustic generator and equalize into a standing sound wave. Formation of the first and second standing sound waves may cause the acoustic reflector to vibrate. The acoustic reflector may be suspended between the two acoustic generators in a fashion that allows for vibration.

An acoustic generator for producing a sound wave may include a speaker. The speaker may include a piezo component. Other suitable components for generating a sound wave may include micro-electromechanical systems ("MEMS"), immersion coils, magnetostatic (ribbon, foil, jet tweeters) loudspeakers, electrostatic loudspeakers, horn drivers, flexural wave transducers, plasma loudspeakers, electromagnetic loudspeakers, exciters or ultrasonic transducers.

Illustrative piezo components may include piezoelectric ultrasonic exciters having a central frequency of 40 kHz and a power level of 90 dB. The piezoelectric ultrasonic exciters may have a circular outline. An illustrative piezoelectric ultrasonic exciter may have a diameter of 1.4 millimeters ("mm"). Piezoelectric ultrasound emitters may be positioned such that they minimize undesired turbulence when the fluid flows through the neutralization chamber through sound waves generated by the emitters.

In some embodiments, sound waves generated by the piezo components may be used to move fluid through the neutralization chamber. For example, generated sound waves may be successively modulated so that the fluid is conveyed through the neutralization chamber. In such embodiments, a generated sound wave may have a propagation direction that corresponds to the desired direction of fluid flow through the neutralization chamber.

The electronic circuitry may generate radiation within the neutralization chamber. The radiation may be light. The radiation may be ultraviolet ("UV") light. The radiation may be UV-C, UV-B or UV-A light. The radiation may be blue or violet light. The radiation may be visible light. The radiation may be infrared light.

For example, the generated radiation may be light having a wavelength greater than 250 nm. The light may have a wavelength greater than 300 nm. The electronic circuitry may include one or more LEDs that generate the light.

The apparatus may include an outlet. The outlet may allow fluid drawn into the neutralization chamber to leave the apparatus. The fluid may be pushed out of the apparatus through the outlet and into the ambient environment. A fan may draw the fluid from the ambient environment into the neutralization chamber. The fan may push the fluid through the neutralization chamber, through the outlet and back into the ambient environment.

The electronic circuitry that generates the acoustic field may include a plurality of piezoelectric components. Particles in the fluid that are moved through the neutralization chamber by the fan are agglomerated by the acoustic field. The piezoelectric components may be speakers that generate sound waves. A plurality of piezoelectric speakers may generate a plurality of standing acoustic waves within the neutralization chamber.

The electronic circuitry may include a circuit board. The circuit board may include an array of piezoelectric speakers. Speakers on the circuit board may be oriented by setting a propagation angle of sound waves generated by the speakers. Speakers on the circuit board may be oriented by arranging the speakers in target positions on the circuit board. Speakers on the circuit board may be oriented by arranging a polarization of the speakers. Speakers may be notched so that a machine can properly orient them.

The circuit board may include an array of LEDs and an array of speakers. The array of LEDs and the array of speakers may be positioned on the circuit board such that acoustophoresis and radiation are simultaneously applied to particles within the fluid, as the fluid passes through the neutralization chamber. The array of light emitting diodes and the array of speakers may be positioned on the circuit board such that acoustophoresis and radiation are applied sequentially to particles within the fluid, as the fluid passes through the neutralization chamber.

It may be preferable to apply radiation simultaneously with or immediately following agglomeration. Applying radiation in close temporal proximity to agglomeration allows the radiation to be applied to the agglomerated particle before any smaller dangling particles may break off a larger agglomerated particle.

Generally, after agglomeration, the now combined smaller particles will remain in the agglomerated state. Smaller particles tend to have electron orbitals (atomic locations where electrons are most likely to be found) on their outside surfaces. This is due to the fact that small particles are predominately defined by their outer surface area. After smaller particles are agglomerated into larger particles, the larger agglomerated particles tend to stay adhered together as a result of "dangling bonds" or other unsatisfied valances that may exist among the smaller (and now agglomerated) particles. The larger agglomerated particles also have more internal volume and therefore bonds are "deeper" within particle and not as easily broken by surface abrasion, movement or contact.

The circuit board may be a first circuit board. The electronic circuitry may include a second circuit board. The second circuit board may include an array of piezoelectric speakers. The second circuit board may include any array of LEDs. The first circuit board may be positioned parallel to the second circuit board.

A first wall of the neutralization chamber may include the first circuit board. A second wall of the neutralization chamber may include the second circuit board. The first circuit board may be positioned a distance of 6-8 centimeters ("cm") apart from the second circuit board. The apparatus may include a housing. The housing may provide support for the inlet. The housing may provide support for the outlet. The housing may protect the electronic circuitry. The housing may define a third wall of the neutralization chamber. The housing may define a fourth wall of the neutralization chamber.

The apparatus may include a fan. The fan may draw fluid into the inlet, push the fluid through the neutralization chamber and out of the outlet. The fan may be capable of moving fluid through the neutralization chamber at a rate of 269:3 m$^3$/h (cubic meters per hour).

As fluid is passed through the neutralization chamber and the acoustic field generated by the electronic circuitry, particles in the fluid that are smaller than 200 nm may be agglomerated into particles larger than 300 nm. As fluid is passed through the acoustic field in the neutralization chamber, particles in the fluid that are smaller than 100 nm may be agglomerated into particles larger than 300 nm. As fluid is passed through the acoustic field in the neutralization chamber, particles in the fluid that are smaller than 50 nm may be agglomerated into particles larger than 300 nm. As fluid is passed through the acoustic field in the neutralization chamber, particles in the fluid that are between 1 nm and 50 nm may be agglomerated into particles larger than 300 nm.

The radiation applied to fluid as the fluid passes through the neutralization chamber may be light having a wavelength greater than 250 nm. The radiation applied to fluid as the fluid passes through the neutralization chamber may be light having a wavelength greater than 280 nm. The radiation applied to fluid as the fluid passes through the neutralization chamber may be light having a wavelength greater than 300 nm.

Applying the radiation to particles in the fluid denatures the particles and renders the particles non-infectious. Because the particles have also been agglomerated, a longer wavelength light may be applied to effectively denature the agglomerated particles. The radiation may denature agglomerated particles by interacting with RNA and/or DNA stands within the agglomerated particles.

Longer wavelength light may have a lower energy level than shorter wavelength light. Applying longer wavelength light may improve energy efficiency of the apparatus. The acoustic field may be oriented to position particles in the fluid for optimal exposure to the radiation. The acoustic field may agglomerate the particles in the fluid and thereby increases the efficacy of denaturation of the agglomerated particles via exposure to the radiation.

The exposure of the particles to radiation may cause the particles to absorb energy. The energy absorption may heat the particles within the fluid and render the particles inactive or non-infectious. The applied radiation may heat particles agglomerated by the acoustic field to a temperature of at least 100° C. For example, applying light to the agglomerated particles may heat the agglomerated particles to a temperature of at least 100° C.

Application of the acoustic field may create agglomerated particles that are more likely to absorb energy in response to applied light. Increasing the rate of absorption increases the temperature of the agglomerated particles in response to light exposure.

Embodiments of the apparatus may not include a filter. Particles that pass though the neutralization chamber may be denaturized and inert. Releasing such particles into the ambient environment may not pose a health risk. Embodiments of the apparatus may include a filter. Embodiments may include two or more filters. The filter may be any suitable filter, or a filter constructed from any suitable material. The filter may prevent particles denaturized within the neutralization chamber from being released into the ambient environment.

The filter may be any suitable filter. For example, the filter may be a HEPA filter. Illustrative filters may include high-performance EPA particle filters, HEPA filters, ULPA high-performance filters, medium filters, tube filters without pressure loss, pre-filters, automotive interior filters, cake filters, crossflow filters, flexible filters, rigid filters, industrial (Siebec) filters, fleeces, backwash filters, water filters, pre-coat filters, room filters, bed filters, magnetic filters, graphene filters, Venturi washers, gas separators, gas scrubbers, SCR catalysts and OCR catalysts. Illustrative filters may be constructed from materials that include etched metals, sintered metals, metal foams, metal threads, metal wool, plastic fabrics, plastic foams, papers, cardboard, cellulose threads, cellulose fabrics, cellulose wools, lignin threads, lignin wools, lignin fabrics, natural fibers, natural wool, natural fiber fabrics, natural fiber, knitted fabrics, natural material foams, sponges, glass fibers, glass wool, glass frits, ceramic fibers, ceramic fabrics, ceramic wool, ceramic foams, boron fibers and stone fibers as well as composite materials of at least two of the aforementioned materials.

In embodiments that include a filter, the filter may be positioned between the neutralization chamber and the outlet. A filter may be positioned inside the neutralization chamber. A filter may be positioned between the inlet and the neutralization chamber. A filter may be integrated into the outlet. A filter may be positioned such that the fluid and agglomerated particles within the fluid are passed through the filter before the fluid is returned to the ambient environment. A filter may be positioned outside the housing.

The outlet may include a grill that is designed to prevent radiation from leaking out of the neutralization chamber. The radiation applied inside the neutralization chamber may have a wavelength of 200 nm-400 nm. The grill may be structured to prevent such light from escaping into the ambient environment. The grill may be structured to allow fluid to pass through the grill at the following rates (cubic meters per hour): 01:20, 02:19, 03:21, 04:16, 05:21, 06:20, 07:19, 08:20, 09:16, 10:16, 11:19, 12:16, 13:14, 14:14, 15:14, 16:13, 17:19, 18:18, 19:19 and/or 20:21. The outlet may be coated with carbon or other light absorbing material to prevent radiation from escaping the neutralization chamber.

A grill shaped like this >>>> may successfully to prevent the escape of light. However, this design is likely to impede a flow of air or other fluid through the grill. A grill shaped like this ⟍⟍⟍ is more advantageous. This longer, and more sloping grill design improves the flow of air or other fluid through the grill. Because light (e.g., in UV spectrum)

may have a wavelength that is shorter relative to the more gradually sloping curvature of the grill, the light will not pass through the grill.

The light waves will contact a surface of the grill and then be reflected to an opposite side of the grill. The light waves may be continuously reflected back and forth within the thickness of the grill, and not pass through the grill into the ambient environment. Coating the grill with carbon or other light absorbing material will further reduce the likelihood of any harmful light, such as UV rays, escaping from the neutralization chamber into the ambient environment.

Methods for denaturing particles in a fluid are provided. Denaturing may include modifying the molecular structure of a particle so as to destroy or diminish biological properties and activity of the particle. The method may include drawing the fluid from an ambient environment into a neutralization chamber. The method may include utilizing a fan to draw air into the neutralization chamber.

Methods may include applying acoustophoresis to agglomerate particles in the fluid. The acoustophoresis may be applied within the neutralization chamber. Methods may include irradiating the agglomerated particles. The irradiating may be performed within the neutralization chamber.

Methods may include irradiating the particles agglomerated by the acoustophoresis with light having a wavelength between 200 nm and 400 nm. The light may be UV-C (e.g., wavelength 200-280 nm), UV-B (e.g., wavelength 280-315 nm) or UV-A (e.g., wavelength 315-400 nm) light.

Methods may include passing the fluid and agglomerated particles through a filter. Methods may include passing the fluid and agglomerated particles through a filter before releasing the fluid and agglomerated particle within the fluid back into the ambient environment. Methods may include releasing the fluid and agglomerated particles back into the ambient environment without passing the fluid through a filter. The agglomerated particles may have been denatured by the radiation before they are released into the ambient environment. Methods may include passing the fluid through a filter before pushing the fluid into the neutralization chamber.

Methods may include drawing the fluid into the neutralization chamber at a rate of $10^{-2}$ mL/sec to $10^{3}$ mL/sec. Methods may include pushing the fluid through the neutralization chamber at a rate of $10^{-2}$ mL/sec to $10^{5}$ mL/sec. Methods may include heating the agglomerated particles within the neutralization chamber to a temperature of at least 100° Celsius ("C"). The irradiating of the agglomerated particles may heat the agglomerated particles to a temperature of at least 100° C.

Applying acoustophoresis to the fluid may agglomerate particles within the fluid. The acoustophoresis may agglomerate particles that are between 1 nm and 50 nm into particles at least 300 nm in size. The acoustophoresis may include generating at least one acoustic field. The at least one acoustic field may be a standing acoustic field.

The at least one standing acoustic field may input 0.25 Watts ("W") to 1 kW of energy into the neutralization chamber. The at least one acoustic filed may have a frequency of 1 kilohertz ("kHz") to 800 megahertz ("MHz") and a power level of 40 to 250 dB. The at least one acoustic field may include at least one ultrasonic wave.

Applying the acoustophoresis may include generating an ultrasonic longitudinal wave and harmonics associated with the ultrasonic longitudinal wave. The ultrasonic longitudinal wave and associated harmonics may be generated within the neutralization chamber as fluid is passing through the neutralization chamber. Applying the acoustophoresis may include generating an ultrasonic transverse wave and harmonics associated with the ultrasonic transverse wave. The ultrasonic transverse wave and associated harmonics may be generated within the neutralization chamber as fluid is passing through the neutralization chamber.

Within the neutralization chamber, methods may include simultaneously irradiating the fluid and applying acoustophoresis. Methods may include first applying acoustophoresis to the fluid and then irradiating the fluid. Methods may include first irradiating the fluid and then applying acoustophoresis to the fluid. Applying acoustophoresis may weaken and destroys outer cell-wall of particles within the fluid. Applying acoustophoresis may include applying ultrasound cavitation. Applying acoustophoresis may suspend particles in the fluid and increase exposure time of the particles to the irradiation.

Applying acoustophoresis may include applying at least one ultrasonic field to the fluid. The at least one ultrasonic field may be generated by at least one pair of opposing exciters. The exciters maybe piezoelectric devices. The at least one ultrasonic field may be generated by at least one exciter-reflector pair. The exciters and reflectors may be oriented inside the neutralization chamber such that an imaginary connecting line between the respective pairs intersect at an angle of 90°. The reflector may be a flat, concave or convex sound reflector.

Apparatus and methods in accordance with this disclosure will now be described in connection with the figures, which form a part hereof. The figures show illustrative features of apparatus and method steps in accordance with the principles of this disclosure. It is to be understood that other embodiments may be utilized, and that structural, functional and procedural modifications may be made without departing from the scope and spirit of the present disclosure.

The steps of methods may be performed in an order other than the order shown and/or described herein. Method embodiments may omit steps shown and/or described in connection with illustrative methods. Method embodiments may include steps that are neither shown nor described in connection with illustrative methods. Illustrative method steps may be combined. For example, an illustrative method may include steps shown in connection with any other illustrative method and/or apparatus described herein.

Apparatus embodiments may omit features shown and/or described in connection with illustrative apparatus. Apparatus embodiments may include features that are neither shown nor described in connection with illustrative apparatus. Features of illustrative apparatus embodiments may be combined. For example, an illustrative apparatus embodiment may include features shown or described in connection with any other illustrative apparatus and/or method embodiment described herein.

FIG. 1 shows illustrative apparatus 100. Apparatus 100 includes housing 101. Apparatus 100 includes outlet 103. Apparatus 100 includes feet 107. Feet 107 may space apparatus 100 away from a surface supporting apparatus 100 by height h. A fluid, such as air, may be drawn along flow lines $f_I$ through the space (having height h) created by feet 107 and into an inlet (not shown) of apparatus 100.

Housing 101 may enclose a neutralization chamber within apparatus 100. Fluid drawn into apparatus 100 may flow into the neutralization chamber. Inside the neutralization chamber, particles within the fluid may be agglomerated and denatured. After the particles are agglomerated and denatured, the fluid may be pushed out of apparatus 100 via outlet 103. FIG. 1 shows fluid being pushed through outlet 103 along flow lines $f_O$.

Apparatus 100 includes illustrative user interface 105. Housing 101 may include a rectangular cut-out designed to accommodate user interface 101. Interface 105 may allow a user to power-on or power-off apparatus 100. Interface 105 may include a power button. Interface 105 may be touch-sensitive. Interface 105 may allow a user to adjust a flow of fluid into apparatus 100. Interface 105 may allow a user to adjust speed of a fan (not shown) positioned within housing 101. Illustrative fan speeds may include 50% speed, 67% speed and 100% speed. At 100% speed, apparatus 100 may draw a maximum quantity of fluid into apparatus 100 along flow lines $f_r$. At 100% speed, apparatus 100 may agglomerate and denature particles within a fluid when the fluid is being drawn into apparatus 100 at rates of 135 cubic meters per hour or 4,757 cubic feet per hour.

In some embodiments, apparatus 100 may include network connectivity. Illustrative network connectivity may include Wi-Fi, Bluetooth or any other wired or wireless communication capabilities. Network connectivity may allow multiple units of apparatus 100 to be linked together. Linking multiple units of apparatus 100 may allow for coordinated agglomeration and denaturing of particles in a fluid by the multiple units of apparatus 100 (e.g., rooms in a hotel).

FIG. 2 shows an illustrative apparatus 200. Apparatus 200 may include one or more properties and features of apparatus 100 (shown in FIG. 1). Apparatus 200 shows inlet 203. Fluid be drawn into apparatus 100 or 200 through inlet 203 along illustrative flow lines $f_I$ (shown in FIG. 1).

Apparatus 200 shows illustrative user interface 201. Interface 201 may include a power button. User interface 201 may be touch-sensitive. User interface 201 may be a touch-sensitive display. User interface 201 may include a screen. The screen may display instructions or current settings of apparatus 201. User interface 201 may display alerts, such as current air quality levels or status information, such as a quantity of fluid processed by apparatus 201 over time.

User interface 201 may display a machine-readable code (e.g., QR code). Scanning the machine-readable code displayed on user interface 201 may allow a user to adjust settings of apparatus 201 via the scanning device. Scanning the machine-readable code displayed on user interface 201 may allow a user to link apparatus 201 to other units. Housing 205 may include a circular cut-out designed to accommodate user interface 201.

FIG. 3 shows exploded view 300 of apparatus 100 (shown in FIG. 1) and apparatus 200 (shown in FIG. 2). Exploded view 300 shows illustrative components of apparatus 100 and 200. Illustrative components include housing 101 (used in connection with apparatus 100) and housing 201 (used in connection with apparatus 200). Illustrative components include user interface 105 (used in connection with apparatus 100) and user interface 201 (used in connection with apparatus 200). Illustrative components include subcomponents 317 of feet 107.

Left air duct 301 and right air duct 303, when assembled within apparatus 100 or 200, may form a neutralization chamber. View 300 shows inlet 203 and outlet 103. Fan housing 305 may provide a base for positioning a fan (not shown) above inlet 203 and below air ducts 301 and 303. The fan may draw fluid from an ambient environment into the neutralization chamber.

View 300 includes circuit boards 307 and 309. Air ducts 301 and 303 may direct fluid drawn through inlet 203 past circuit boards 307 and 309. Circuit board 307 may be affixed to left air duct 301. Circuit board 309 may be affixed to right air duct 303. Circuit boards 307 and 309 may include sound emitters. The sound emitters may generate sound waves that agglomerate particles in a fluid flowing through the neutralization chamber. Circuit boards 307 and 309 may include LEDs. The LEDs may emit light that denatures particles in a fluid flowing through the neutralization chamber.

Light emitted by the LEDs may be ultraviolet ("UV") radiation. View 300 shows that UV reflector 311 may be mounted on left air duct 301. UV reflector 311 may prevent leakage of UV light (e.g., emitted by LEDs on circuit board 309) out of apparatus 100 or 200. View 300 shows that UV reflector 313 may be mounted on right air duct 303. UV reflector 313 may prevent leakage of UV light (e.g., emitted by LEDs on circuit board 307) out of apparatus 100 or 200.

FIG. 4 shows illustrative view 400 of circuit boards 307 and 309 (shown in FIG. 3). View 400 shows that circuit boards 307 and 309 are positioned opposite and parallel to each other. View 400 shows sound emitters 401 on circuit board 307. View 400 shows LEDs 403 on circuit board 307.

View 400 shows illustrative sound wave 411 generated by sound emitter 405 on circuit board 309. View 400 shows illustrative sound wave 413. In some embodiments, sound wave 413 may be generated by sound emitter 407 on circuit board 307. In some embodiments, sound wave 413 may be generated by an acoustic reflector mounted on circuit board 307. Circuit boards 307 and 309 may be oriented such that sound emitters 405 and 407 are aligned opposite to each other. Sound emitters 405 and 407 may be configured to generate sound waves that having phases that differ by 180° or any suitable value. View 400 shows that sound waves 411 and 413 have phases that differ by 180°. Sound waves 411 and 413 may collectively form a standing sound wave.

View 400 shows that nodes 409 are formed at an intersection of sound waves 411 and 413. Nodes 409 may be low pressure points relative to antinodes 415 and 417. Relatively lower pressure at nodes 409 may cause agglomeration of particles within a fluid flowing past circuit boards 307 and 309 and through sound waves 411 and 413. Each of sound emitters 401 may be aligned with and thereby paired to a corresponding sound emitter on circuit board 309. Each pair of sound emitters may produce sound waves and associated nodes that agglomerate particles in the fluid, as the fluid flows through a neutralization chamber and past circuit boards 307 and 309.

Particles agglomerated by sound waves 411 and 413 may be exposed to light generated by LEDs 403. Circuit board 309 may also include LEDs (not shown). In some embodiments (not shown), LEDs may be positioned on a circuit board such that particles in the fluid are exposed to light before the particles are agglomerated. In some embodiments (not shown), LEDs may be interspersed between sound emitters 401 such that particles in the fluid are exposed to light after passing through a sound wave generated by a first pair of sound emitters (e.g., 407 and 405) and before passing through a second sound wave generated by a second pair of sound emitters (e.g., 408 and 406).

FIG. 5 shows an illustrative schematic view 500 of fluid flow through a neutralization chamber. View 500 shows that fluid is drawn into an inlet from an ambient environment outside the neutralization chamber. View 500 shows that the neutralization chamber is defined, at least in part, by two opposing and parallel circuit boards. Each of the circuit boards may include sound emitters that agglomerate particles within the fluid. Each of the circuit boards may include LEDs or other light sources that denature particles in the fluid. View 500 shows that after passing through neutralization chamber, the fluid is returned to the ambient environment via an outlet. Fluid returned to the ambient environment may include agglomerated and denatured particles.

Figure 3:
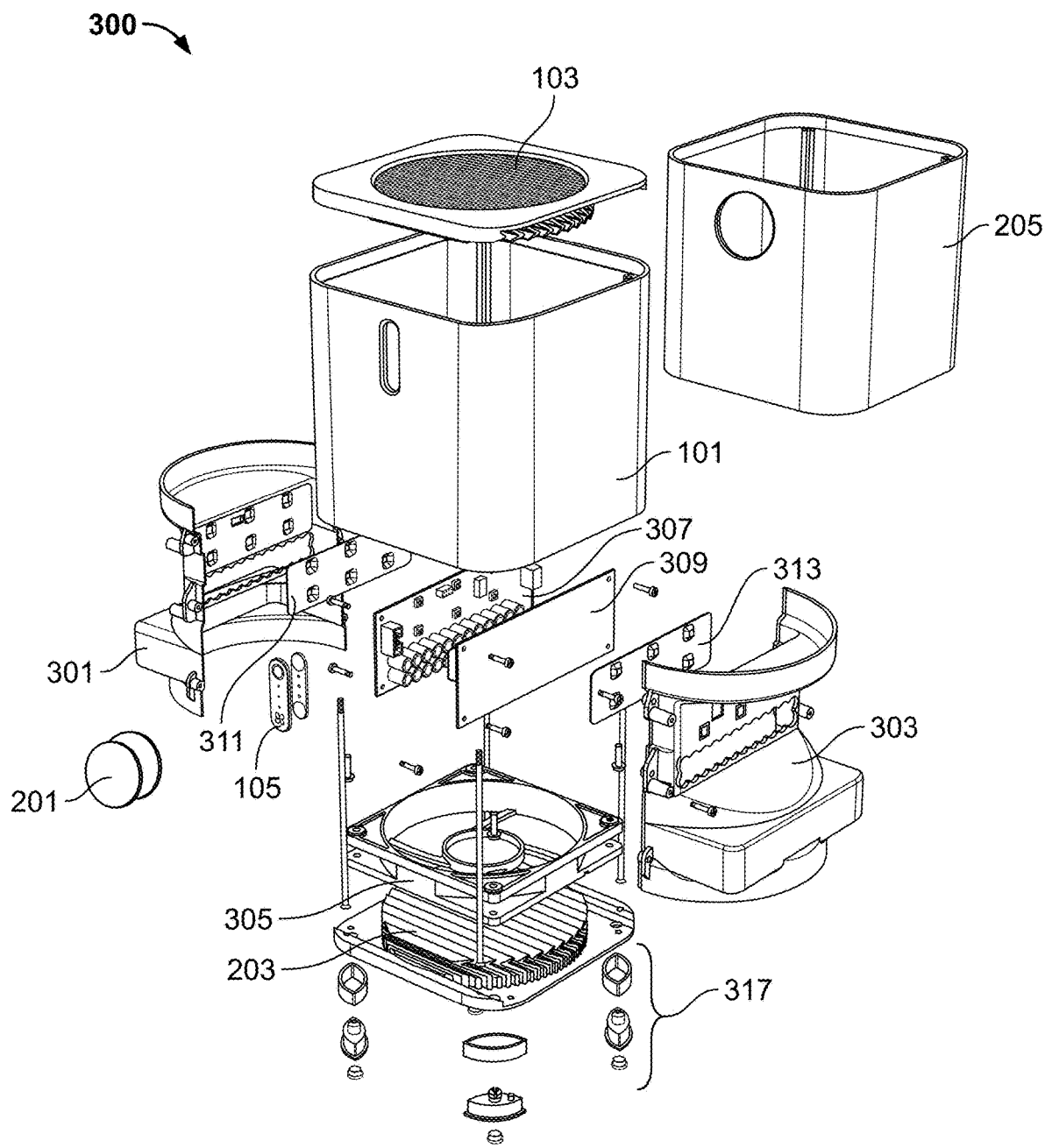
FIG. 3 shows illustrative apparatus in accordance with principles of the disclosure.
Figure 4:
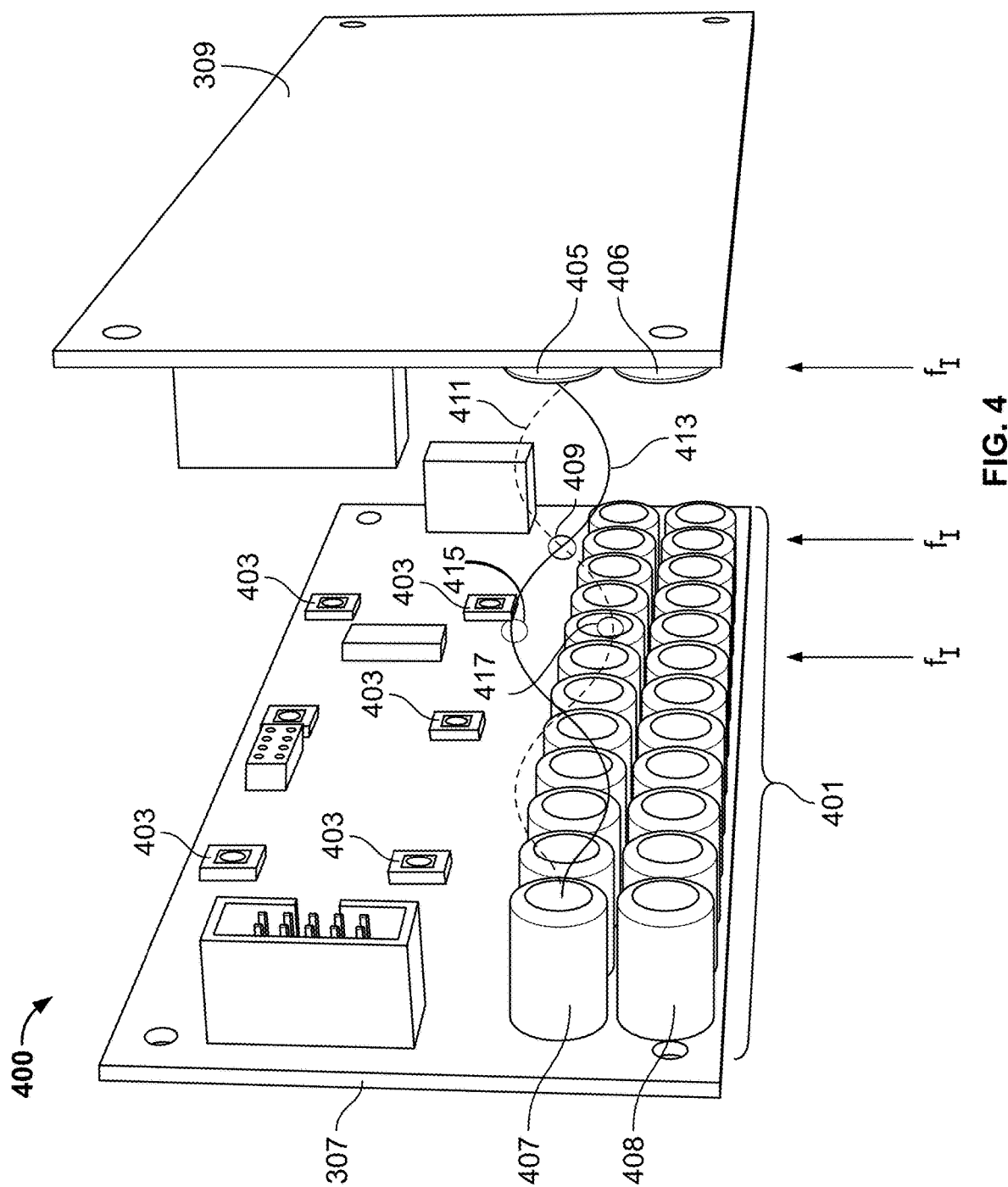
FIG. 4 shows illustrative apparatus in accordance with principles of the disclosure.
Figure 5:
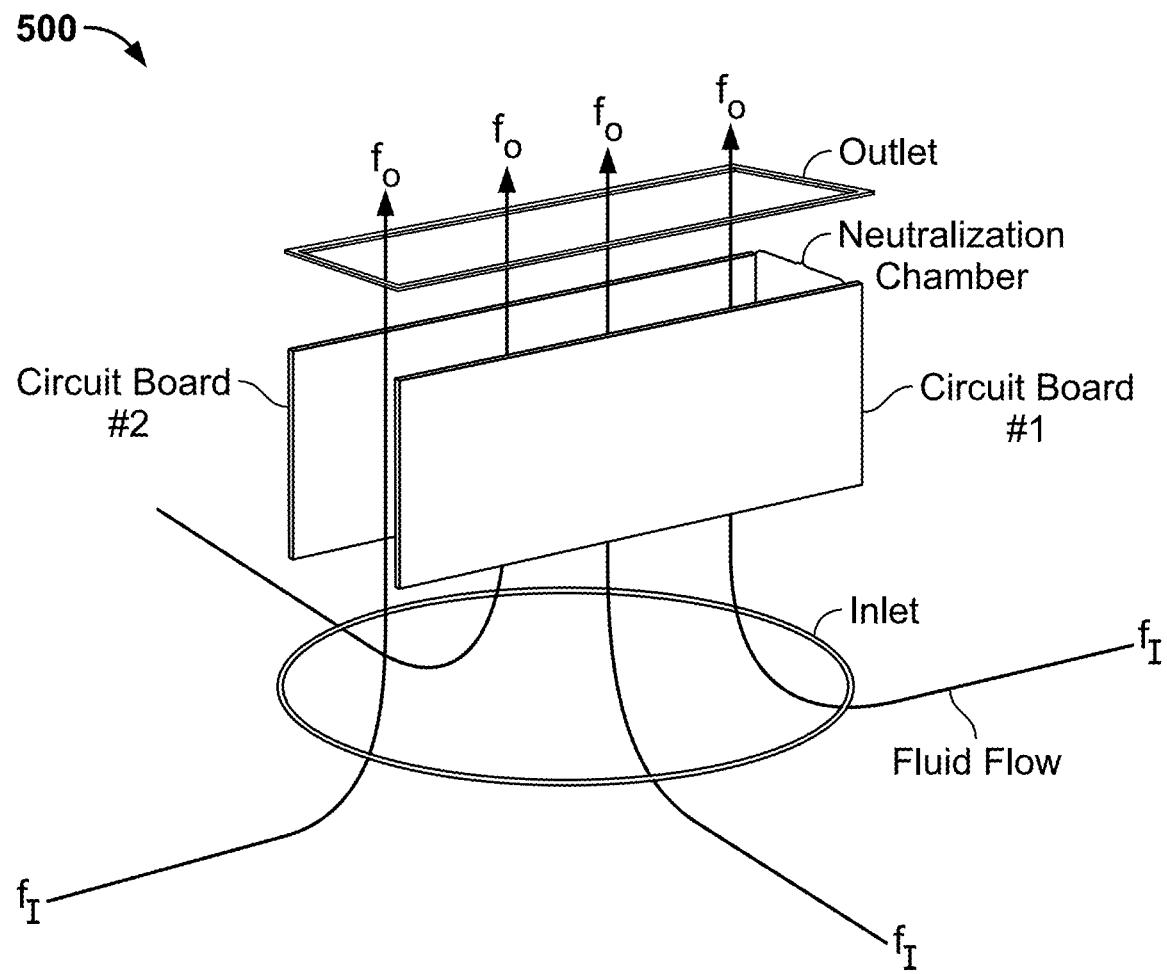
FIG. 5 shows illustrative apparatus in accordance with principles of the disclosure.
Figure 6:
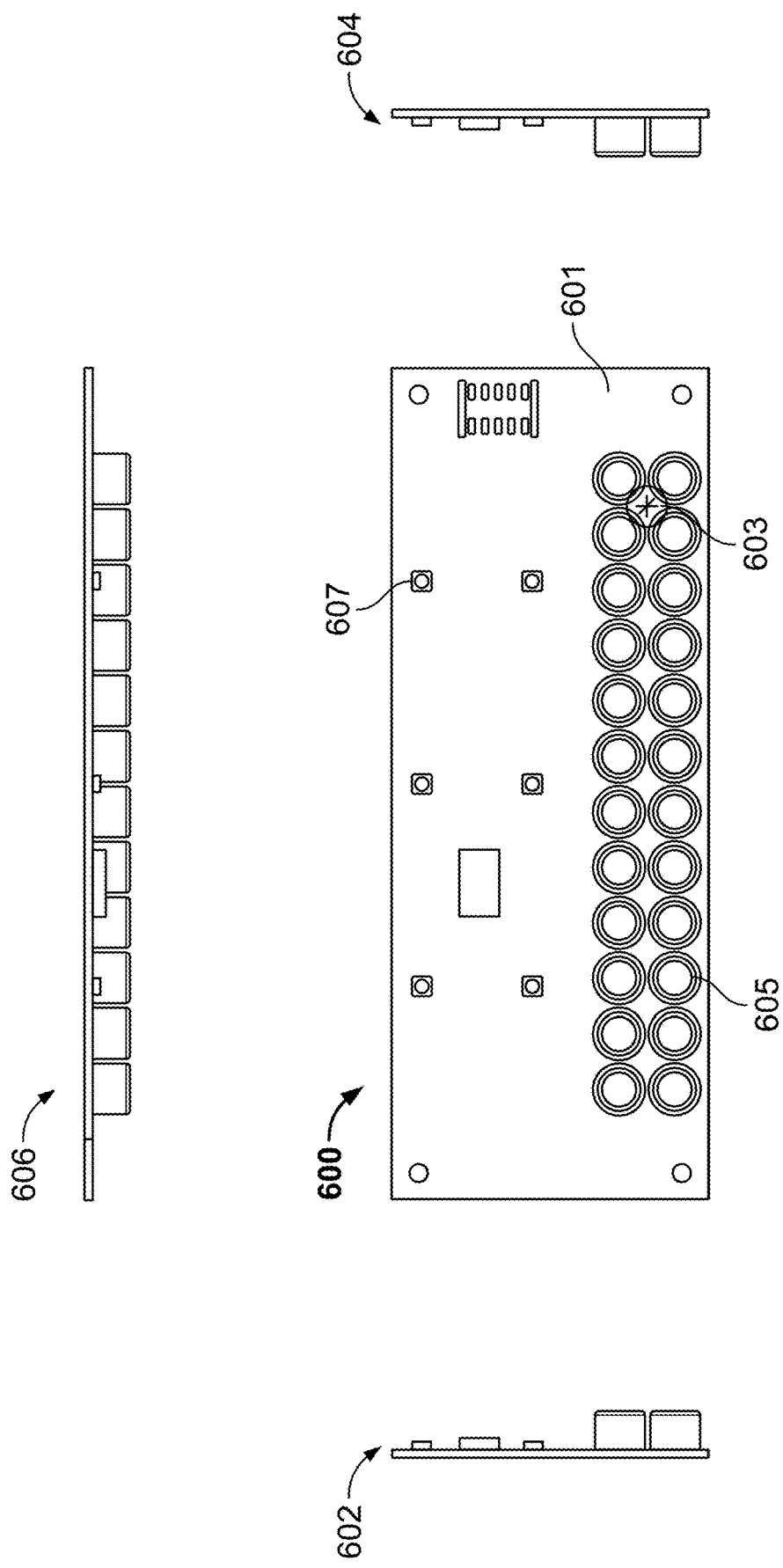
FIG. 6 shows illustrative apparatus in accordance with principles of the disclosure.

FIG. 6 shows illustrative front plan view 600 of circuit board 601. Circuit boards 307 and 309 (shown in FIGS. 3 and 4) may include one or more features of circuit board 601. Circuit board 601 includes sound emitters 605. Sound emitters 605 may be piezoelectric speakers. Circuit board 601 includes light sources 607. Light sources 607 may be LEDs. In other embodiments, circuit board 601 may include light sources at locations 603.

FIG. 6 shows left side view 602 of circuit board 601. FIG. 6 shows right side view 604 of circuit board 601. FIG. 6 shows top view 606 of circuit board 601.

Figure 7:
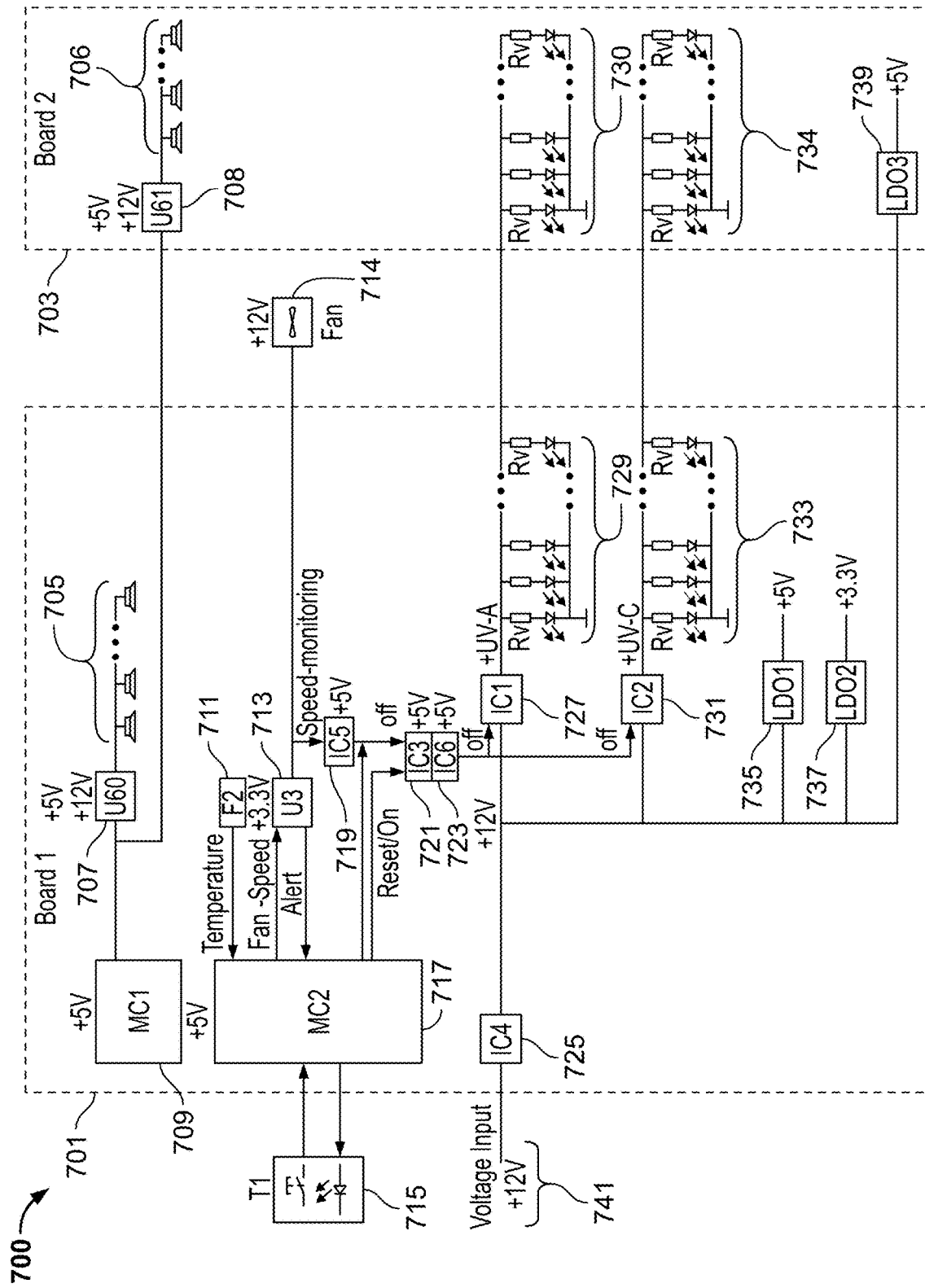
FIG. 7 shows illustrative apparatus in accordance with principles of the disclosure.
Figure 8C:
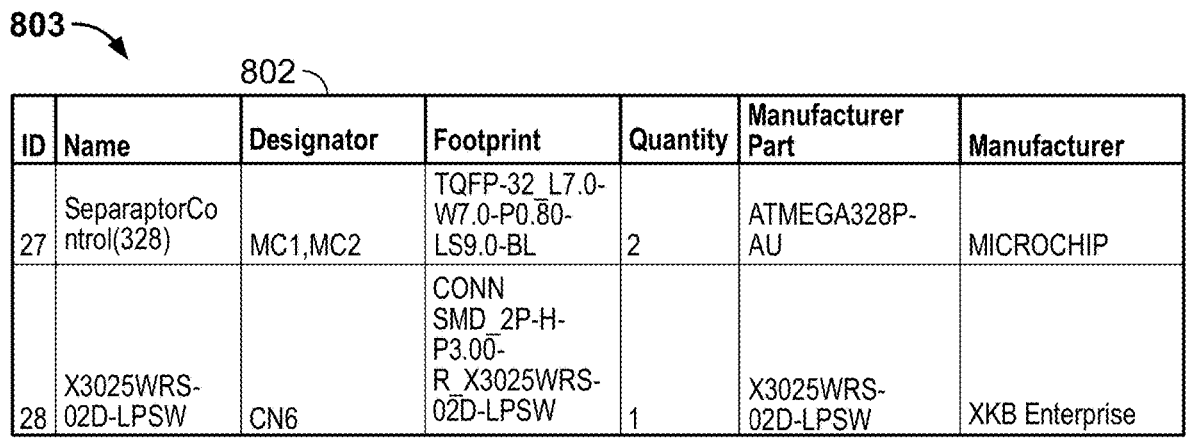
Figure 9:
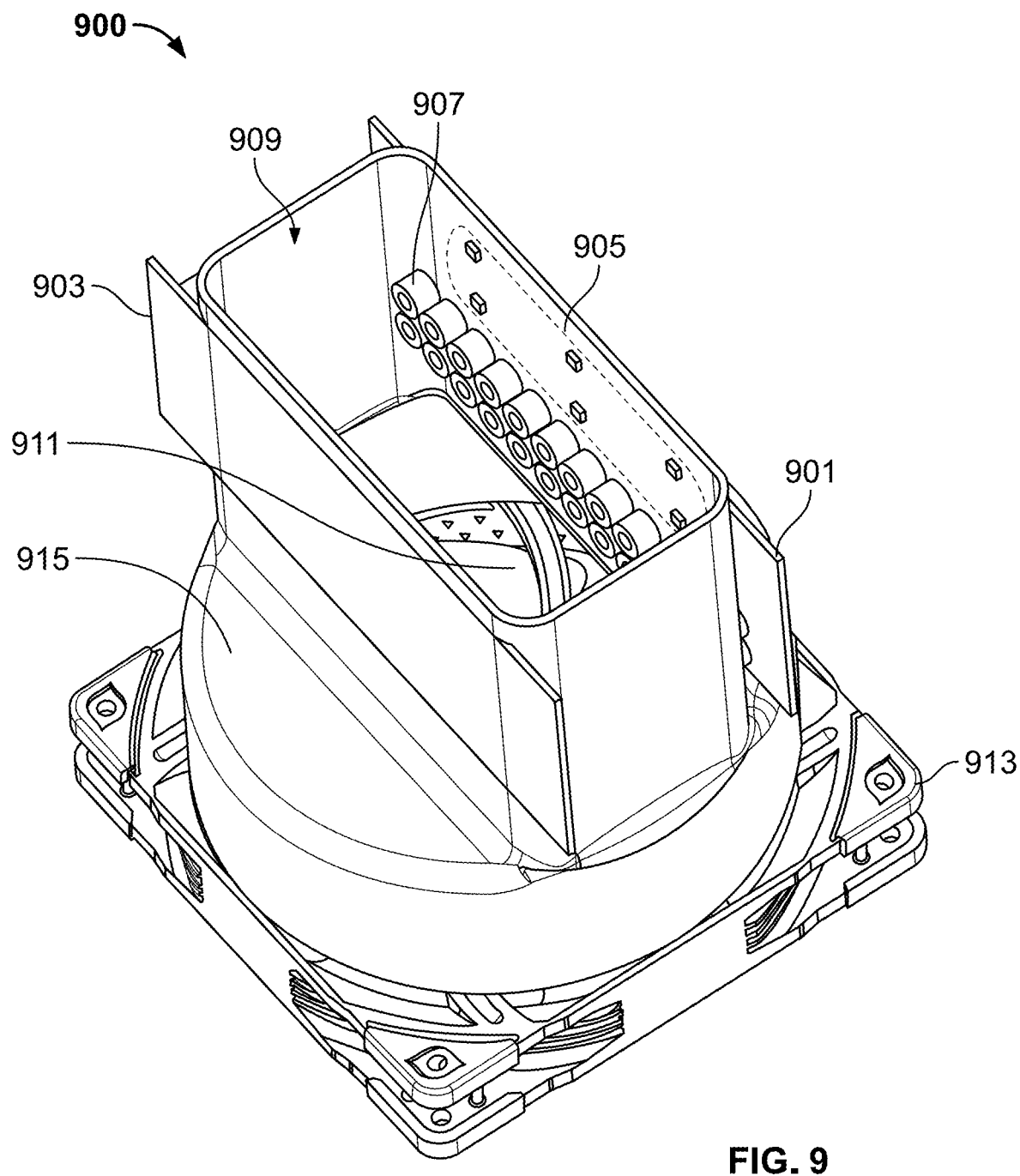
FIG. 9 shows illustrative apparatus in accordance with principles of the disclosure.

FIG. 7 shows illustrative electronic circuitry 700. Electronic circuitry 700 includes circuit boards 701 and 703. Electronic circuitry 700 includes control button 715. Control button 715 may include an LED indicator light. Control button 715 may be used to activate or deactivate circuit boards 701 and 703. Control button 715 may activate circuit boards 701 and 703 by supplying power to circuit boards 701 and 703. Control button 715 may deactivate circuit boards 701 and 703 by cutting off power to circuit boards 701 and 703.

Power for electronic circuitry 700 may be provided by voltage input 741. Reverse polarity protection circuit 725 protects electronic circuitry 700 from damage when a polarity of power supplied to circuit boards 701 and 703 is reversed. Electronic circuitry 700 includes voltage regulators 727, 731, 735, 737 and 739. A voltage regular maintains voltage applied to an electrical component within predefined limits. The voltage regulators protect electrical components from being damaged by fluctuations in supplied electrical voltage.

Voltage regulator 735 maintains a 5-volt power supply for components of circuit board 701. Voltage regulator 737 maintains a 3.3-volt power supply for components of circuit board 701. Voltage regulator 739 maintains a 5-volt power supply for components of circuit board 703. Voltage regulator 727 maintains 12-volt power supplied to LEDs 729 and 730. Voltage regulator 731 maintains 12-volt power supplied to LEDs 733 and 734.

Circuit board 701 includes microcontrollers 709 and 717. In some embodiments, microcontrollers 709 and 717 may be a single integrated circuit. In some embodiments, microcontroller 717 may control operation of microcontroller 709. Microcontrollers 709 and 717 may be integrated circuits that each includes a processor circuit (e.g., transistors that implement Boolean logic gates), memory and input/output ("I/O") connections. The I/O connections may receive input signals. The processor circuit may utilize the inputs signals (e.g., from control button 715 or temperature sensor 711) to generate an output signal. The output signal may then be transmitted to another device or system component that takes action or performs a function based on the output signal.

Microcontroller 709 controls operation of piezo-drivers 707 and 708. Piezo-driver 707 instructs sound emitters 705 on circuit board 701 to produce sound waves. Piezo-driver 708 instructs sound emitters 706 on circuit board 703 to produce sound waves. For example, microcontroller 709 may provide instruction to piezo-driver 707 that result in the production of sound waves by sound emitters 705 that have a target phase, frequency or power.

Circuit boards 701 and 703 may be positioned in a neutralization chamber. A fluid may be directed to flow through the neutralization chamber between circuit boards 701 and 703. Sound waves produced by sound emitters 705 and 706 may agglomerate particles within the fluid, as the fluid flows through the neutralization chamber.

Microcontroller 717 may control operation of LEDs 729, 730, 733 and 734. In some embodiments, microcontroller 717 may also control sound emitters 705 and 706 by controlling operation of microcontroller 709. Microcontroller 717 receives input from temperature sensor 711. Temperature sensor 711 may monitor temperature of LEDs 729, 730, 733 and 734. Temperature sensor 711 may monitor temperature of fluid within a neutralization chamber. Based on input received from temperature sensor 711, microcontroller 717 may issue instructions to LED controllers 721 and 723 to activate or deactivate LEDs 729, 730, 733 and 734. Based on input received from temperature sensor 711, microcontroller 717 may activate or deactivate sound emitters 705 and/or 706.

Microcontroller 717 provides an output signal to fan controller 713. Fan controller 713 may control activation and deactivation of fan 714. Fan 714 draws fluid into a neutralization chamber. Activating fan 714 may include setting a rotational speed of fan 714. Changing a rotational speed of fan 714 changes the rate at which fluid is drawn into a neutralization chamber. Speed controller 719 may monitor rotational speed of fan 714.

Fan controller 713 may generate an alert that is provided as an input signal to microcontroller 717. Microcontroller 717 may issue output signals to fan controller 713 based on received alerts. For example, in response to detecting a malfunction of fan 714, microcontroller 717 may deactivate LEDs 729, 730, 733 and/or 734. In response to detecting a malfunction of fan 714, microcontroller 717 may deactivate sound emitters 705 and/or 706.

Electronic circuitry 700 includes LEDs 729 and 730. LEDs 729 and 730 emit UV-A (e.g., wavelength 315-400 nm) light. Electronic circuitry 700 includes LEDs 733 and 734. LEDs 733 and 734 emit UV-C (e.g., wavelength 200-280 nm) light. In other embodiments, electronic circuitry 700 may include LEDs that emit radiation having any target wavelength. For example, electronic circuitry may include LEDs that emit UV-B light (e.g., wavelength 280-315 nm) or light having any wavelength greater than 250 nm.

Electronic circuitry 700 includes LED controllers 721 and 723. LED controllers 721 and 723 may activate or deactivate LEDs 729, 730, 733 and/or 734. Microcontroller 717 may issue output signals to LED controllers 721 and 723.

FIGS. 8A-8C show illustrative detail for components that may be utilized to construct electronic circuitry 700 (shown in FIG. 7). "Designator" column 802 in FIGS. 8A-8C includes component labels shown in FIG. 7 that correlate component details 800, 801 and 803 to the circuit board components labels shown in FIG. 7. In addition to illustrative components details 800, 801 and 803, Molex 430450809 may be used as an alternative for component CN3 (see, e.g., row #4 in FIG. 8A) and Molex 436500213 may be used as an alternative to component CN6 (see, e.g., row #28 in FIG. 8C).

FIG. 9 shows neutralization chamber 909 positioned above fan 911. Neutralization chamber 909 and fan 911 may be present within apparatus 100 (shown in FIG. 1) or 200 (shown in FIG. 2). Fan 911 is mounted within fan housing 913. Fan 911 may draw fluid from an ambient environment outside neutralization chamber 909. Fluid may be directed into neutralization chamber 909 by air duct 915.

Circuit boards 901 and 903 may apply one or more sound waves to fluid within neutralization chamber 909. The sound waves may be generated by sound emitters 907. The sound waves may agglomerate particles within the fluid. Circuit boards 901 and 903 may apply light to fluid within neutralization chamber 909. The light may be generated by LEDs 905. Light emitted by LEDs 905 may denature particles within the fluid.

Figure 2:
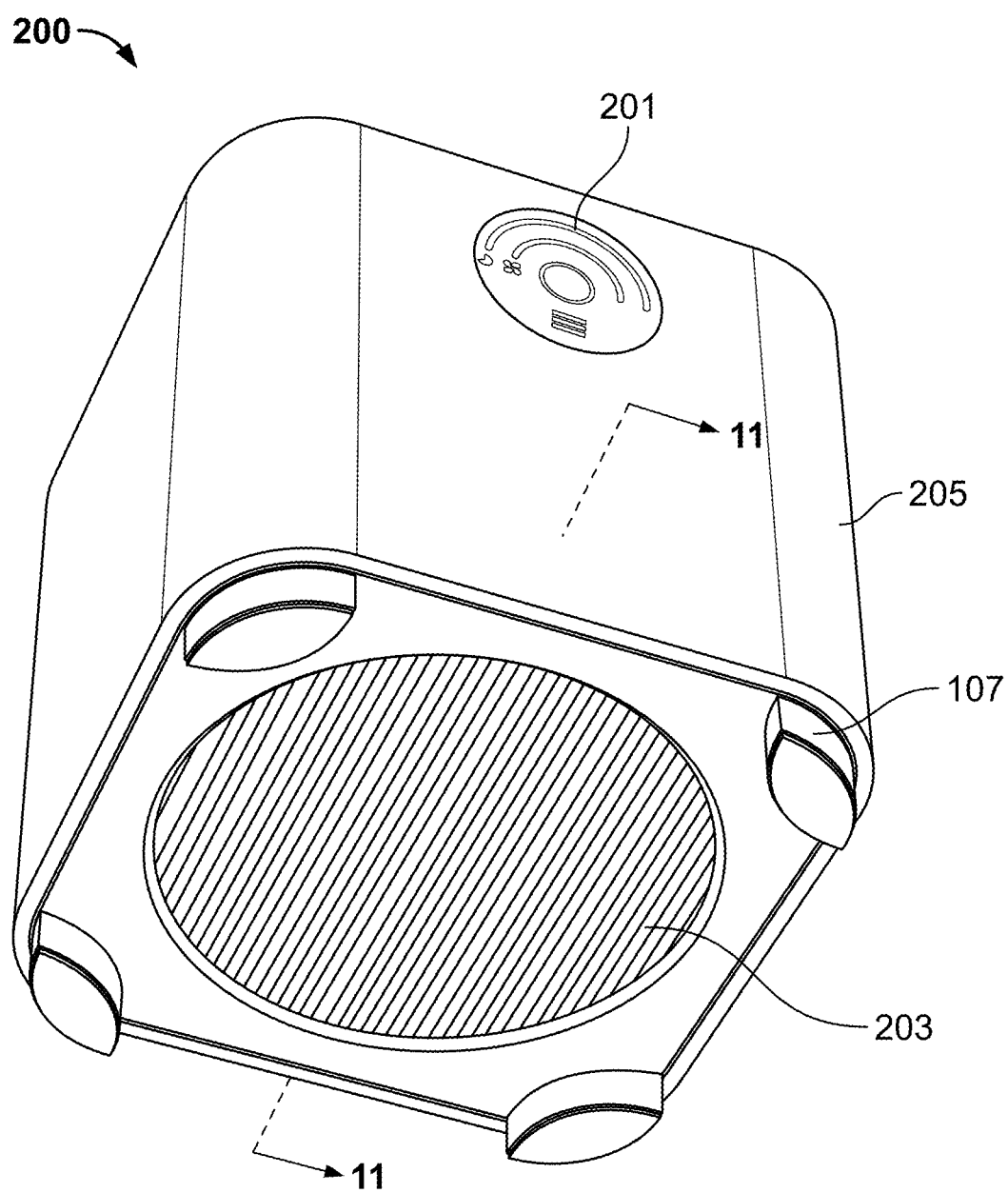
FIG. 2 shows an illustrative apparatus in accordance with principles of the disclosure.
Figure 10:
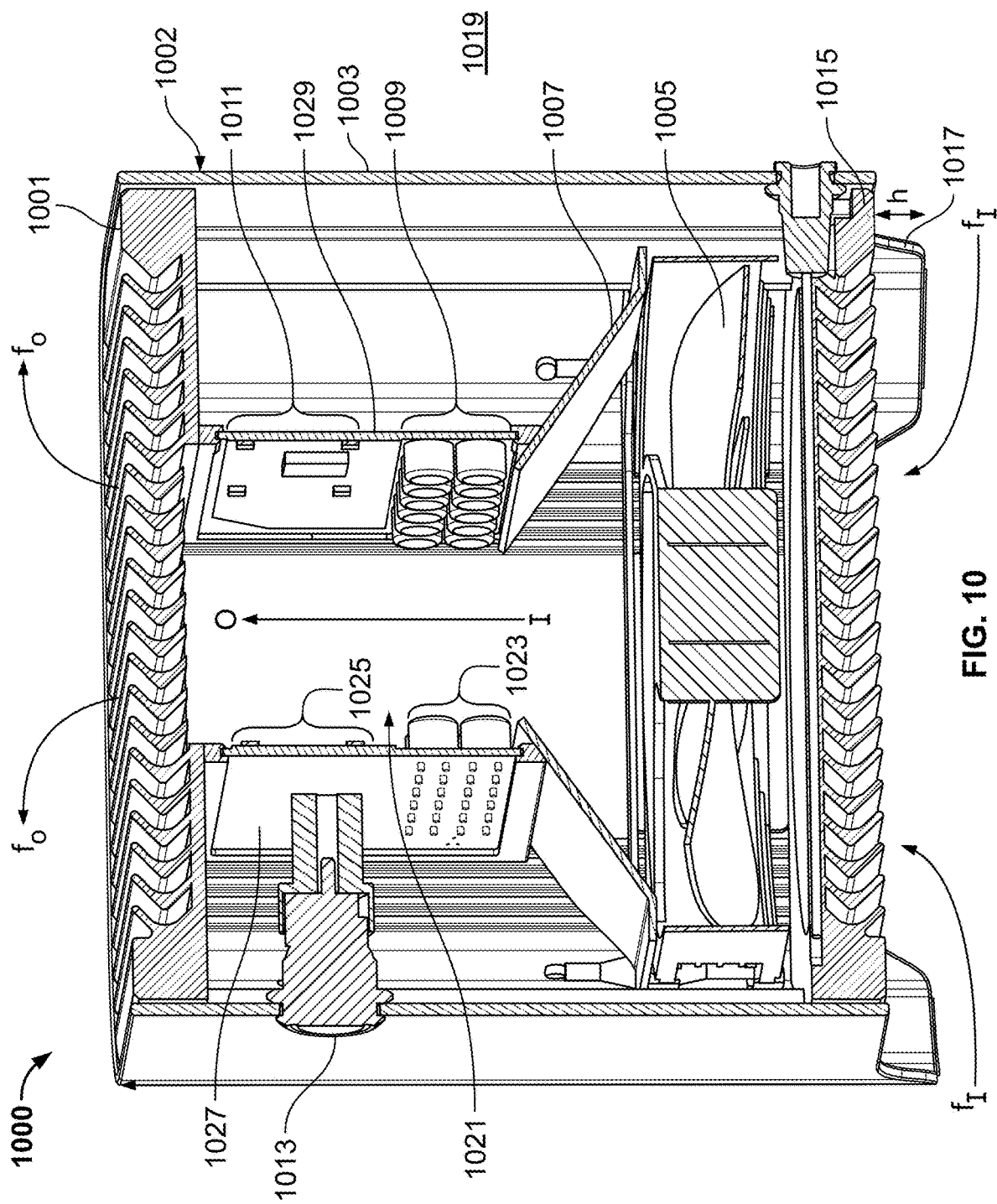
FIG. 10 shows illustrative apparatus in accordance with principles of the disclosure.

FIG. 10 shows illustrative cross-section 1000 of apparatus 1002. Apparatus 1002 may include one or more features of apparatus 100 (shown in FIG. 1) and apparatus 200 (shown in FIG. 2). Cross-section 1000 is taken of apparatus 1002 along cut lines 10-10 shown in FIG. 1 with respect to apparatus 100. Apparatus 1002 includes control button 1013. Apparatus 1002 includes housing 1003.

Cross-section 1000 shows that fan 1005 draws fluid from ambient environment 1019 through inlet 1015 and into neutralization chamber 1021. Feet 1017 space inlet 1015 apart from a surface supporting apparatus 1002 by height h. Fluid may be drawn into neutralization chamber 1021 along flow lines $f_I$. Cross-section 1000 also shows that, within apparatus 1002, ducts 1007 guide fluid to flow past circuit boards 1027 and 1029.

As fluid flows through neutralization chamber 1021 from I to O, sound emitters 1009 and 1023 apply an acoustic field that agglomerates particles in the fluid. Sound emitters 1009 are mounted on circuit board 1029. Sound emitters 1023 are mounted on circuit board 1027. As fluid flows through neutralization chamber 1021 from I to O, LEDs 1011 and 1025 apply light that denatures particles in the fluid. LEDs 1011 are mounted on circuit board 1029. LEDs 1025 are mounted on circuit board 1027.

One of circuit boards 1027 or 1029 may be a "primary" circuit board that controls operation of both circuit board 1027 and circuit board 1029. For example, circuit board 1027 may include microcontroller 717 (shown in FIG. 7).

Fan 1005 pushes fluid out of apparatus 1002 and back into ambient environment 1019 through outlet 1001. Fluid may flow out of outlet 1019 along flow lines $f_O$. Fluid flowing out of outlet 1001 may include larger particles than fluid drawn into apparatus 1002 through inlet 1015. Fluid flowing out of outlet 1001 may include more denatured particles than fluid drawn into apparatus 1002 through inlet 1015.

Figure 11:
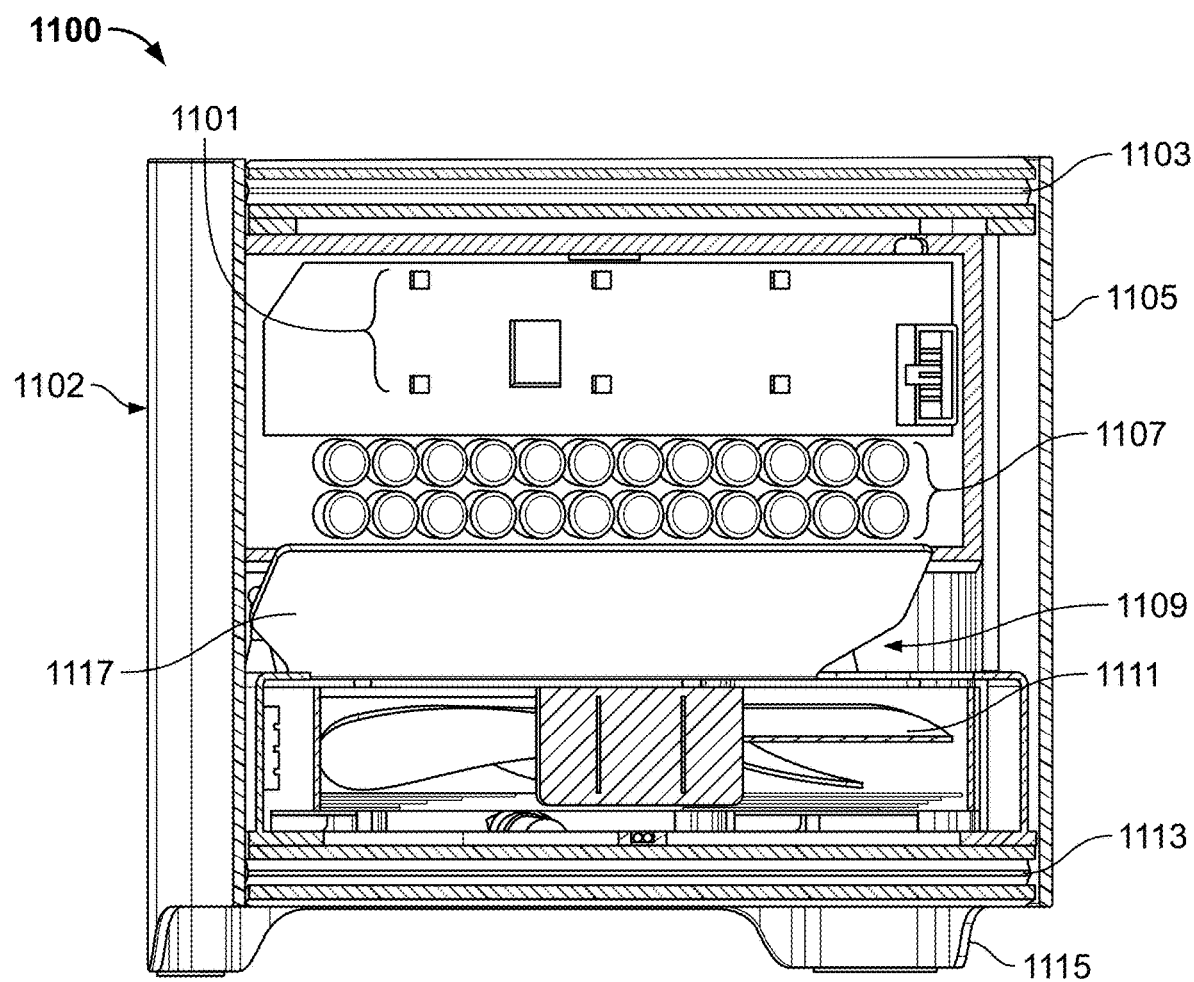
FIG. 11 shows illustrative apparatus in accordance with principles of the disclosure.

FIG. 11 shows illustrative cross-section 1100 of apparatus 1102. Cross-section 1100 is taken of apparatus 1102 along cut lines 11-11 shown in FIG. 2 with respect to apparatus 200. Cross-section 1100 shows array of LEDs 1101. Cross-section 1100 shows array of sound emitters 1107. Array of LEDs 1101 and array of sound emitters 1107 may be part of a circuit board.

Cross-section 1100 shows neutralization chamber 1109. Neutralization chamber 1109 is bounded on a first side by duct 1117, LEDs 1101 and sound emitters 1107. Neutralization chamber 1109 is bounded on a second and third side by housing 1105. Neutralization chamber 1109 may be bounded on a fourth side (not shown) by another duct, another array of LEDs and/or another array of sound emitters.

Cross-section 1101 shows feet 1115. Feet 1115 may space apparatus 1102 apart from a surface that supports apparatus 1102. Fan 1111 may rotate and draw fluid from an ambient environment, into a space between apparatus 1102 and the surface supporting apparatus 1102. Fan 1111 may draw fluid into neutralization chamber 1109 through inlet 1113. Fan 1111 may push fluid within neutralization chamber 1109 past sound emitters 1107. As the fluid flows through neutralization chamber 1109, sound emitters 1107 may generate an acoustic field that agglomerates particles within the fluid. As the fluid flows through neutralization chamber 1109, LEDs 1101 may radiate light that denatures particles within the fluid. Fan 1111 may push fluid out of neutralization chamber 1109 and back into the ambient environment through outlet 1103.

Figure 12:
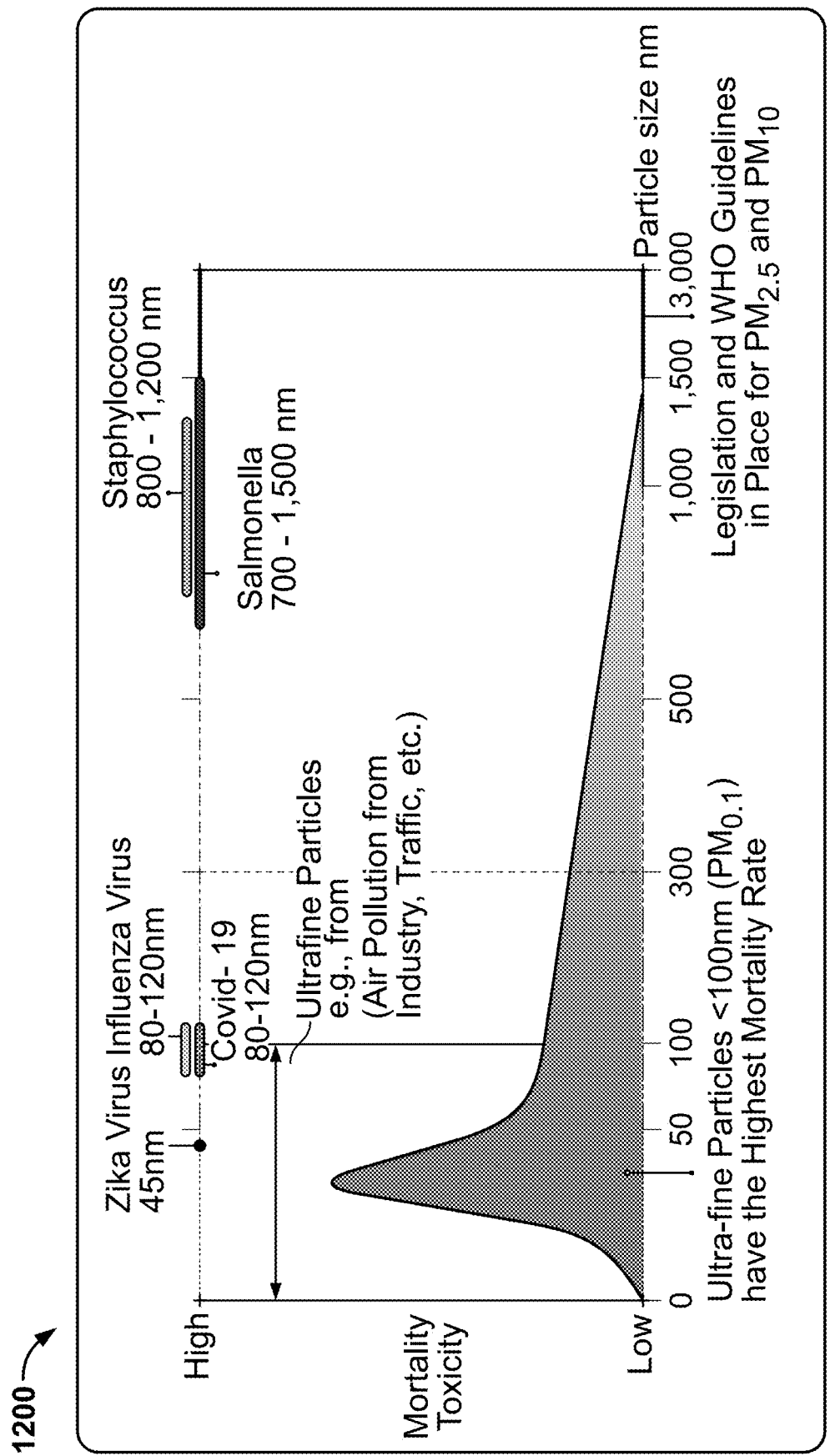
FIG. 12 shows illustrative information in accordance with principles of the disclosure.

FIG. 12 shows illustrative particle sizes 1200. Particle sizes 1200 shows that ultra-fine particles having sizes<100 nm are associated with a higher degree of toxicity than larger particles. Apparatus and methods described herein may be utilized to agglomerate and denature ultra-fine particles having sizes<100 nm.

Figure 13:
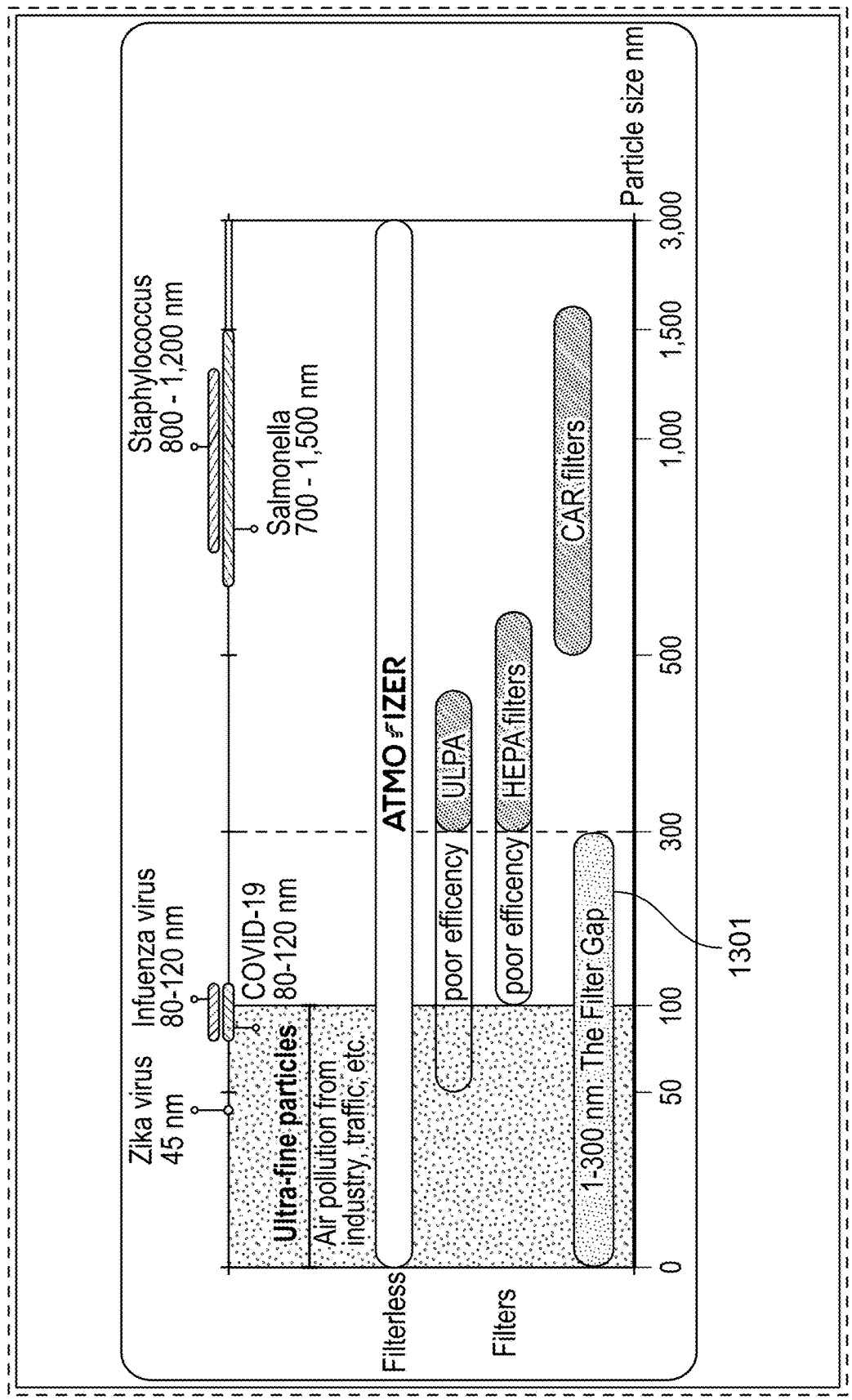
FIG. 13 shows illustrative information in accordance with principles of the disclosure.

FIG. 13 shows illustrative particle removal metrics 1300. Metrics 1300 show that ULPA and HEPA filters are optimally used for removal of particles having sizes≥300 nm. Metrics 1300 show that apparatus and method disclosed herein and offered under the Atmofizer mark are capable of removing pathogenic particles≤300 nm and even pathogenic particles≤100 nm. Metrics 1300 show that apparatus and method disclosed herein and offered under the Atmofizer mark therefore close "filter gap" 1301.

Figure 14:
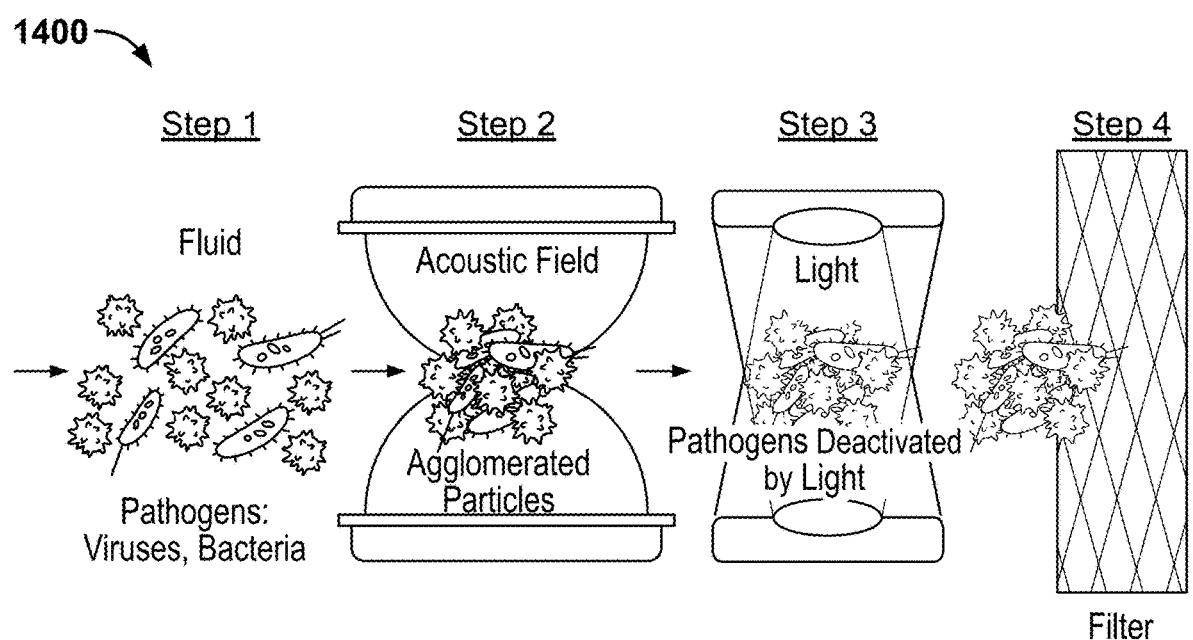
FIG. 14 shows an illustrative process in accordance with principles of the disclosure.

FIG. 14 shows illustrative process 1400 for aggregating, neutralizing and filtering ultra-fine particles in a fluid. Process 1400 may be performed by apparatus described herein. Process 1400 begins at step 1. At step 1, a fluid such as air or water, contains pathogenic particles including virus and bacteria. At step 2, the fluid is passed through an acoustic field. The acoustic field may include nodes and antinodes. For example, the acoustic field may include one or more standing sound waves. Particles in the fluid may be agglomerated at nodes of the standing sound wave.

At step 3, the agglomerated particles are exposed to light. The light may be ultraviolet light. For example, the light may be UV-C light. The agglomerated particles may be simultaneously exposed to light having two or more different wavelengths. For example, a single LED circuit may emit UV-C light and UV-A light. The light may denature the agglomerated (and non-agglomerated) particles in the fluid. The light may be more effective to denature agglomerated particles compared to non-agglomerated particles. The light may deactivate pathogens in the fluid.

At step 4, the fluid may optionally be passed through a filter. The filter may be a HEPA or ULPA filter. The filter may remove agglomerated particles. The fluid may be passed through the filter before being released into an ambient environment. Because at step 4 particles in the fluid have been agglomerated, a more porous filter (e.g., for filtering particles>400 nm) may be used effectively. A more porous filter may require less energy to push air or other fluids through the filter.

In some embodiments (not shown), fluid may be passed through a filter before agglomeration at step 2 and before being exposed to light at step 3.

Figure 15:
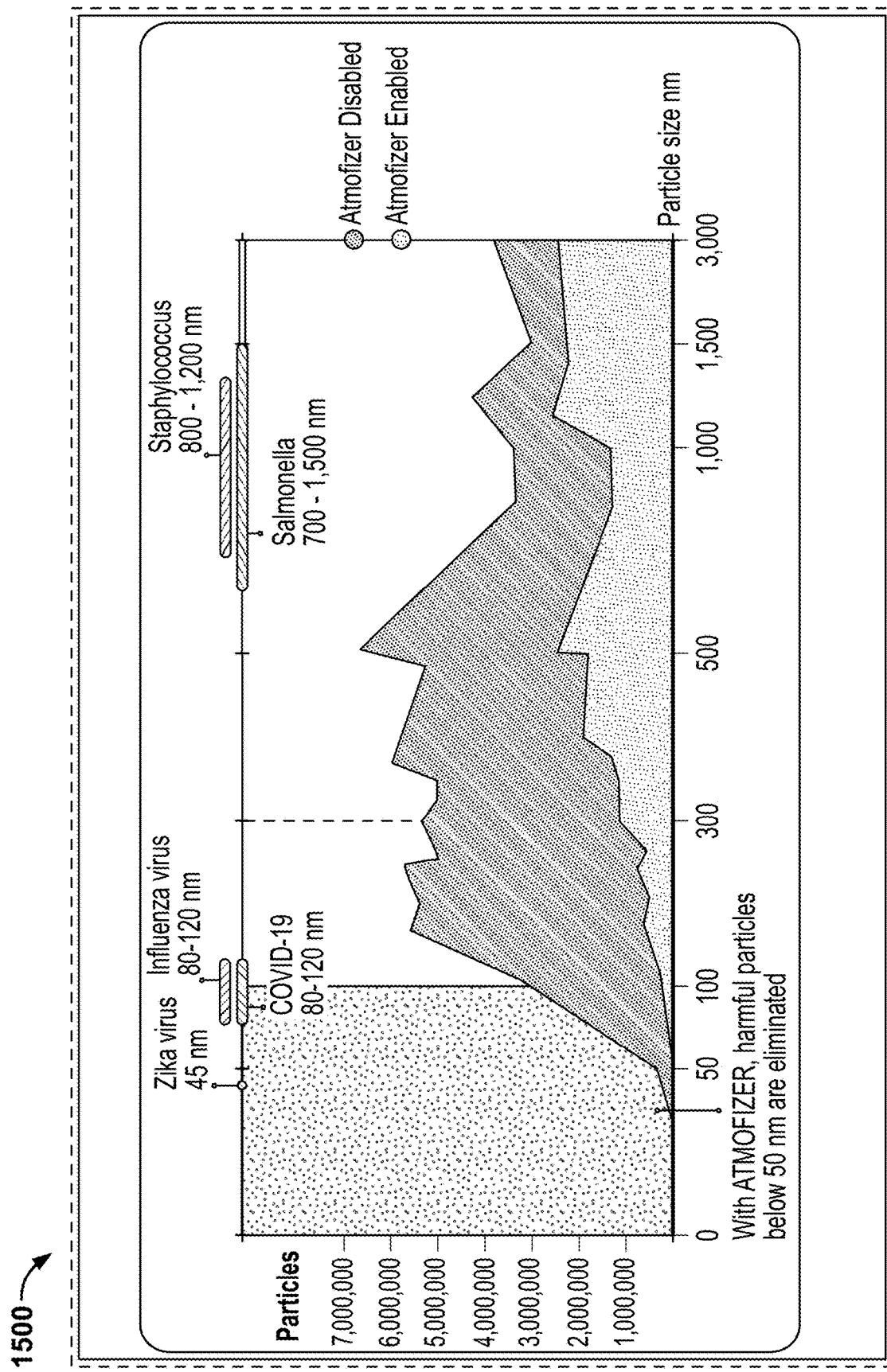
FIG. 15 shows illustrative information in accordance with principles of the disclosure.

FIG. 15 shows an illustrative graphical representation 1500 of the efficacy of apparatus and methods described herein and offered under the Atmofizer mark for agglomerating and denaturing particles in a fluid. Graphical representation 1500 shows that apparatus and methods described herein and offered under the Atmofizer mark are effective to denature particles 50 nm. Graphical representation 1500 shows that apparatus and methods described herein and offered under the Atmofizer mark are effective to denature particles 100 nm. Graphical representation 1500 shows that apparatus and methods described herein and offered under the Atmofizer mark are more effective to denature particles relative to other fluid filtration techniques.

Thus, apparatus and methods for ULTRA-FINE PARTICLE AGGREGATION, NEUTRALIZATION AND FILTRATION have been provided. Persons skilled in the art will appreciate that the present disclosure can be practiced by other than the described embodiments, which are presented for purposes of illustration rather than of limitation. The present disclosure is limited only by the claims that follow.

What is claimed is:

1. An apparatus for denaturing particles in a fluid, the apparatus comprising:
   a neutralization chamber;
   an inlet that allows the fluid to enter the neutralization chamber;
   electronic circuitry that generates:
      an acoustic field that agglomerates particles within the neutralization chamber; and
      light that denatures particles within the neutralization chamber; and
   a fan that draws the fluid through the inlet and moves the fluid into the neutralization chamber;
wherein the electronic circuitry comprises:
   a first array of piezoelectric speakers;
   a second array of piezoelectric speakers;
   a first array of light emitting diodes ("LEDs"); and
   a second array of LEDs; and
wherein:
   a first circuit board comprises the first array of piezoelectric speakers and the first array of LEDs;
   a second circuit board comprises the second array of piezoelectric speakers and the second array of LEDs; and
   the first circuit board is spaced apart from the second circuit board by a distance of 6-8 centimeters ("cm").

2. The apparatus of claim 1, wherein the electronic circuitry generates a plurality of standing acoustic waves within the neutralization chamber.

3. The apparatus of claim 1, wherein the first and second arrays of LEDs and the first and second arrays of piezoelectric speakers are positioned within the neutralization chamber such that the acoustic field and the light are applied to particles within the fluid as the fluid moves through the neutralization chamber.

4. The apparatus of claim 1, wherein the acoustic field agglomerates particles within the fluid that are smaller than 100 nm into particles larger than 300 nm.

5. The apparatus of claim 1, wherein the first and second arrays of LEDs generate light having a wavelength greater than 250 nm.

6. The apparatus of claim 1, wherein the electronic circuitry generates light that denatures particles agglomerated by the acoustic field.

7. The apparatus of claim 1, wherein the light heats particles agglomerated by the acoustic field to a temperature of at least 100° Celsius.

8. The apparatus of claim 1, further comprising a filter positioned between the first or second arrays of LEDs and an outlet that allows the fluid to leave the neutralization chamber.

9. The apparatus of claim 1, further comprising an array of acoustic reflectors positioned opposite the first or second array of piezoelectric speakers; wherein, at least one acoustic reflector in the array of acoustic reflectors is aligned with at least one piezoelectric speaker in the first or second array of piezoelectric speakers such that at least one standing sound wave is formable between the at least one acoustic reflector and the at least one piezoelectric speaker.

10. The apparatus of claim 1, wherein a first piezoelectric speaker in the first array of piezoelectric speakers is aligned with a second piezoelectric speaker in the second array of piezoelectric speakers such that a standing sound wave is formable between the first and second piezoelectric speakers.

11. A method for denaturing particles in a fluid, the method comprising:
   drawing the fluid from an ambient environment into a neutralization chamber;
   within the neutralization chamber:
      generating an acoustic field using a first array of piezoelectric speakers on a first circuit board and a second array of piezoelectric speakers on a second circuit board;
      applying the acoustic field to agglomerate particles in the fluid;
      generating a first light using a first array of light emitting diodes ("LEDs") on the first circuit board;
      generating a second light using a second array of LEDs on the second circuit board; and
      applying the first light and the second light to denature the agglomerated particles;
wherein, the first circuit board is spaced apart from the second circuit board by a distance of 6-8 centimeters ("cm").

12. The method of claim 11, wherein the light has a wavelength between 200 nanometers ("nm") and 400 nm.

13. The method of claim 11, further comprising passing the fluid through a filter before pushing the fluid drawn into the neutralization chamber back into the ambient environment.

14. The method of claim 11, further comprising pushing the agglomerated particles into the ambient environment without passing the fluid drawn into the neutralization chamber through a filter.

15. The method of claim 11, wherein applying the acoustic field comprises exposing the fluid to a standing sound wave having a power level of 40 to 250 decibels ("dB") and a frequency of 1 kilohertz ("kHz") to 800 megahertz ("MHz").

* * * * *